(12) United States Patent
Hacker et al.

(10) Patent No.: US 12,194,279 B2
(45) Date of Patent: Jan. 14, 2025

(54) MEDICAMENT DELIVERY DEVICE

(71) Applicant: medmix Switzerland AG, Haag (CH)

(72) Inventors: Gerd Hacker, Pforzheim (DE); Joachim Keitel, Esslingen (DE)

(73) Assignee: medmix Switzerland AG, Haag (CH)

( * ) Notice: Subject to any disclaimer, the term of this patent is extended or adjusted under 35 U.S.C. 154(b) by 0 days.

(21) Appl. No.: 17/828,618

(22) Filed: May 31, 2022

(65) Prior Publication Data

US 2022/0362468 A1 Nov. 17, 2022

Related U.S. Application Data

(60) Division of application No. 17/021,787, filed on Sep. 15, 2020, which is a continuation of application No. PCT/EP2019/059150, filed on Apr. 10, 2019.

(Continued)

(51) Int. Cl.
   *A61M 5/19* (2006.01)
   *A61M 5/24* (2006.01)
   *A61M 5/315* (2006.01)

(52) U.S. Cl.
   CPC .............. *A61M 5/19* (2013.01); *A61M 5/24* (2013.01); *A61M 5/31551* (2013.01); *A61M 5/3158* (2013.01); *A61M 2005/2492* (2013.01)

(58) Field of Classification Search
   CPC ... A61M 5/19; A61M 5/31543; A61M 5/2448
   See application file for complete search history.

(56) References Cited

U.S. PATENT DOCUMENTS

| 4,968,299 A * | 11/1990 | Ahlstrand ........... A61M 5/2448 D24/114 |
| 4,973,318 A | 11/1990 | Holm et al. |

(Continued)

FOREIGN PATENT DOCUMENTS

| CN | 105530973 A | 4/2016 |
| CN | 105579085 A | 5/2016 |

(Continued)

OTHER PUBLICATIONS

International Search Report and Written Opinion issued Jul. 10, 2019 in corresponding International Application No. PCT/EP2019/059150.

(Continued)

*Primary Examiner* — Dung T Ulsh
(74) *Attorney, Agent, or Firm* — Global IP Counselors, LLP

(57) ABSTRACT

A medicament delivery device for a mixing process to create a therapeutic substance for delivery within a multi-chambered cartridge, the delivery device includes a distal part with a dose setting mechanism having a housing, a dose setting knob, an injection button, a piston rod capable of moving axially along the longitudinal axis of the housing during dose delivery, and a return ring configured to reset the piston rod to a starting position. The delivery device also includes a proximal part including a cartridge holder configured to accept a multi-chambered cartridge, the cartridge holder including a screw driven sleeve configured for attachment to the distal part and rotation of the screw driven sleeve performing a medicament mixing process within the multi-chambered cartridge.

27 Claims, 17 Drawing Sheets

Related U.S. Application Data

(60) Provisional application No. 62/688,153, filed on Jun. 21, 2018, provisional application No. 62/657,283, filed on Apr. 13, 2018.

(56) References Cited

U.S. PATENT DOCUMENTS

| | | |
|---|---|---|
| 6,319,225 B1 * | 11/2001 | Sugita ............... A61M 5/2448 604/82 |
| 7,976,509 B2 | 7/2011 | Moser et al. |
| 10,420,893 B2 | 9/2019 | Bayer et al. |
| 10,569,024 B2 | 2/2020 | Harms et al. |
| 2005/0165349 A1 | 7/2005 | Stamp |
| 2012/0107783 A1 | 5/2012 | Julian et al. |
| 2012/0277683 A1 | 11/2012 | Moller |
| 2012/0283659 A1 | 11/2012 | Kouyoumjian et al. |
| 2013/0313823 A1 * | 11/2013 | Holmqvist .......... A61M 5/3129 285/330 |
| 2014/0236093 A1 * | 8/2014 | Eggert ............. A61M 5/14546 29/428 |
| 2014/0350480 A1 | 11/2014 | Keitel |
| 2015/0157803 A1 | 6/2015 | Radmer et al. |
| 2016/0015904 A1 | 1/2016 | Plumptre et al. |
| 2016/0263320 A1 | 9/2016 | Constantineau et al. |
| 2018/0169343 A1 * | 6/2018 | Rolfe ................. A61M 5/3148 |
| 2019/0015595 A1 | 1/2019 | Keitel |
| 2019/0117898 A1 | 4/2019 | Hirschel et al. |
| 2019/0167903 A1 | 6/2019 | Staub et al. |
| 2020/0023136 A1 | 1/2020 | Keitel et al. |
| 2020/0164150 A1 | 5/2020 | Smith et al. |
| 2020/0282147 A1 | 9/2020 | Quinn et al. |
| 2020/0289762 A1 | 9/2020 | Keitel |
| 2020/0376205 A1 | 12/2020 | Keitel |
| 2020/0405958 A1 | 12/2020 | Hacker et al. |
| 2022/0072233 A1 | 3/2022 | Karlsson et al. |
| 2022/0118192 A1 | 4/2022 | Keitel |

FOREIGN PATENT DOCUMENTS

| | | |
|---|---|---|
| DE | 102006004561 A1 | 7/2007 |
| EP | 0562029 B1 | 7/1999 |
| EP | 1066847 B1 | 6/2004 |
| EP | 2283886 A2 | 2/2011 |
| EP | 3181170 A1 | 6/2017 |
| WO | 9210425 A1 | 6/1992 |
| WO | 2009014955 A2 | 1/2009 |
| WO | 2009092807 A1 | 7/2009 |
| WO | 2009114542 A1 | 9/2009 |
| WO | 2012105898 A1 | 8/2012 |
| WO | 2015090320 A2 | 6/2015 |
| WO | 2016198540 A2 | 12/2016 |
| WO | 2018018166 A1 | 2/2018 |
| WO | 2019197493 A1 | 10/2019 |
| WO | 2021214272 A1 | 10/2021 |

OTHER PUBLICATIONS

Chinese Office Action issued Jan. 27, 2022 in corresponding Chinese Application No. 201980025424.4.
European Search Report issued Aug. 3, 2022 in corresponding European Application No. 22171651.7.
European Search Report issued Oct. 6, 2022 in corresponding European Application No. 221703424.4.
Written Opinion and International Search Report dated Jul. 10, 2019 of International Application No. PCT/EP2019/059150.
International Search Report and Written Opinion issued Jul. 26, 2023 in International Application No. PCT/EP2023/061187.
European Search Report issued Dec. 13, 2022 in European Application No. 22184328.7.
International Search Report and Written Opinion issued Jul. 26, 2023 in International Application No. PCT/EP2023/061175.
International Search Report and Written Opinion issued Jul. 26, 2023 in International Application No. PCT/EP2023/061173.
European Search Report issued Oct. 6, 2022 in European Application No. 22170342.4.
European Search Report issued Nov. 23, 2022 in European Application No. 22180552.6.
International Search Report and Written Opinion issued May 17, 2023 in International Application No. PCT/EP2023/061183.
European Search Report issued Dec. 2, 2022 in European Application No. 22183157.1.
International Search Report and Written Opinion issued Jul. 14, 2023 in International Application No. PCT/EP2023/061193.
International Search Report and Written Opinion issued May 23, 2023 in International Application No. PCT/EP2023/061184.
Chinese Office Action issued Jan. 24, 2024 in corresponding Chinese Application 202210758244.0 (Google machine translation).

* cited by examiner

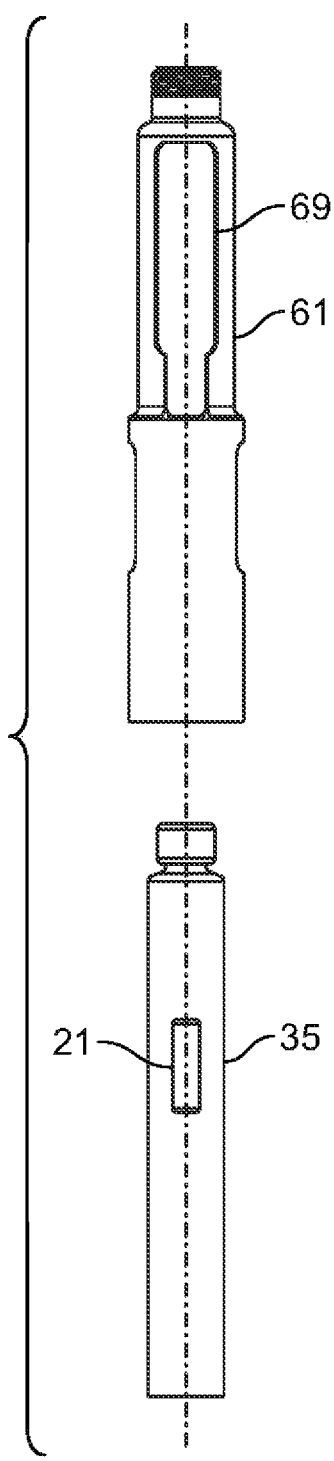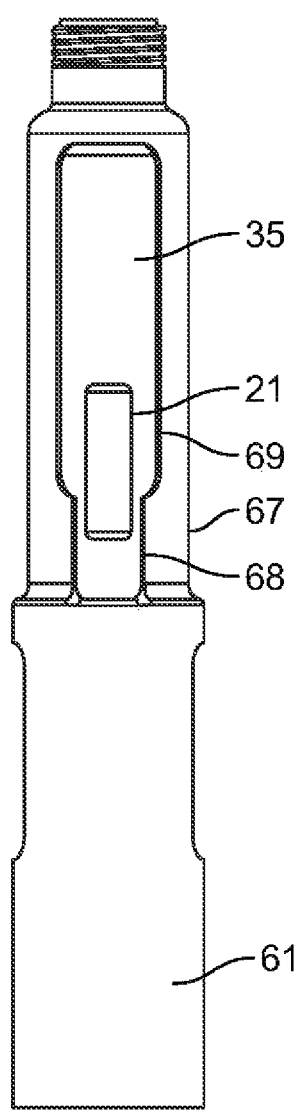

zero position dose set start of injection end of injection

FIG. 12C  FIG. 12B  FIG. 12A
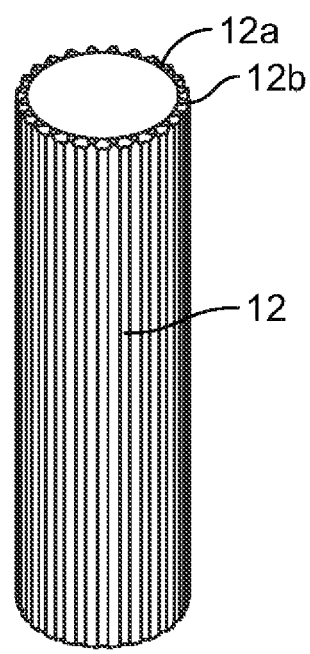
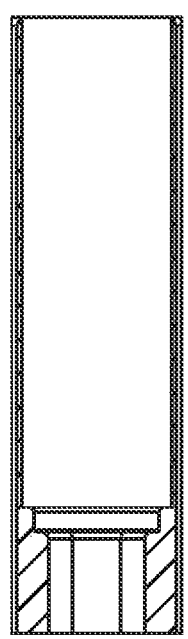
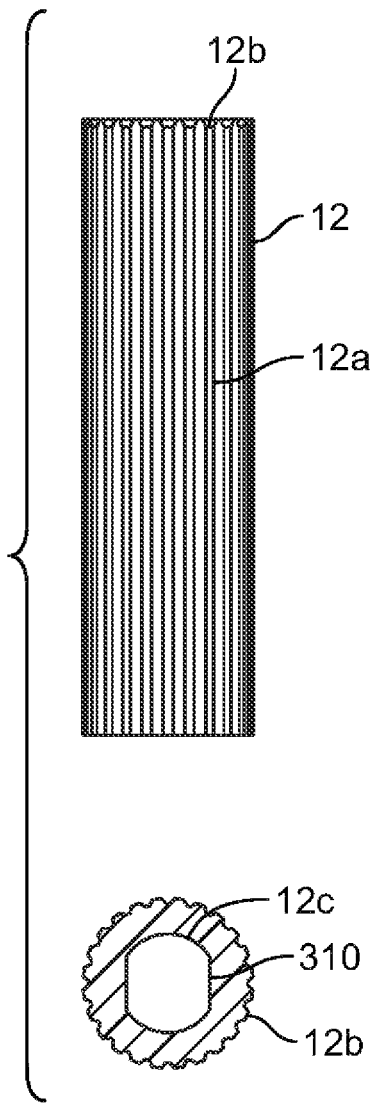
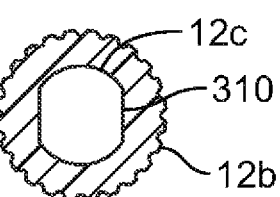
FIG. 12D

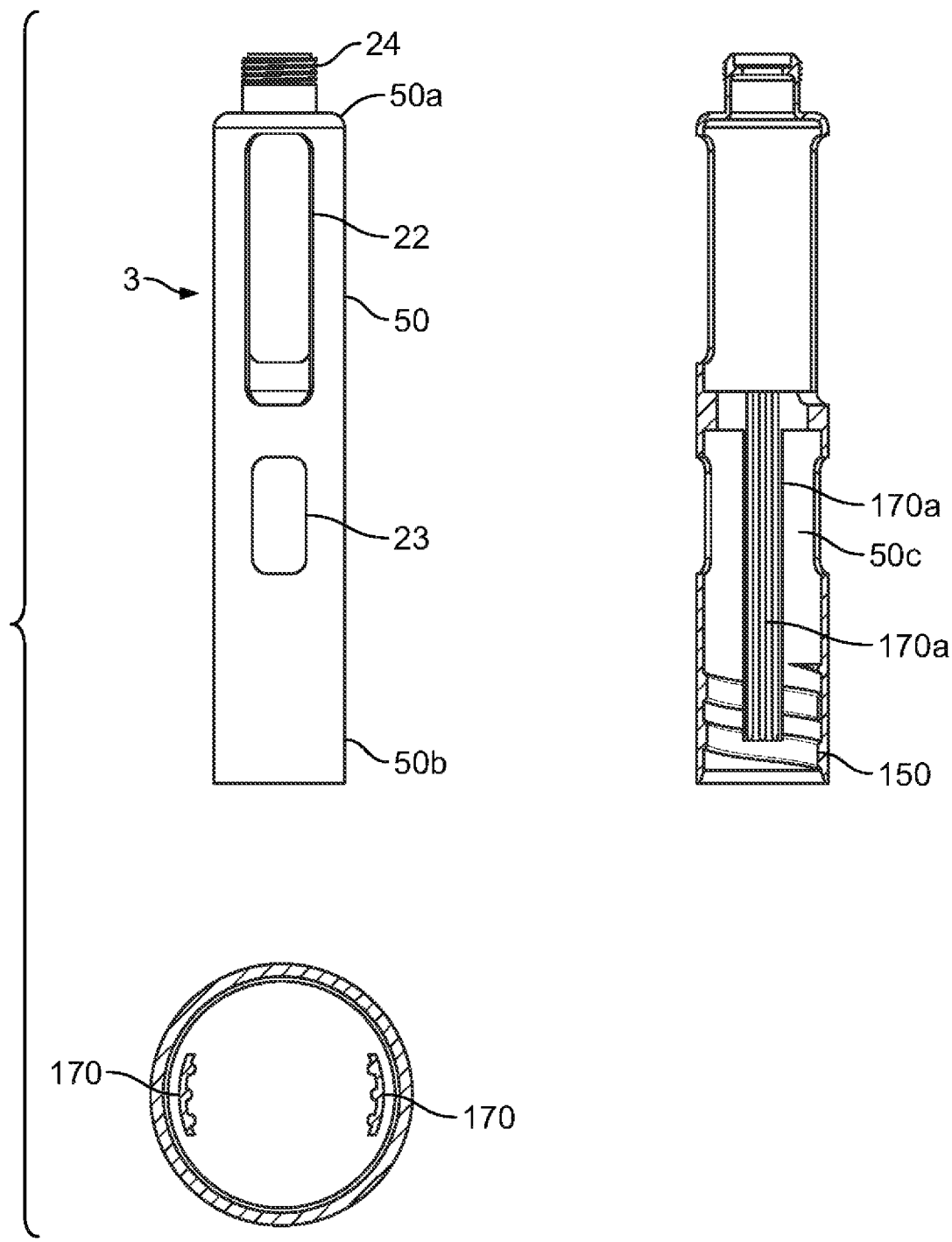

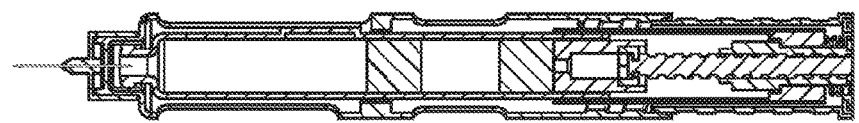
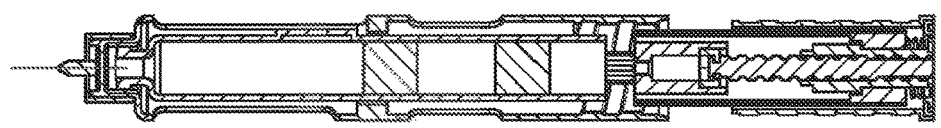
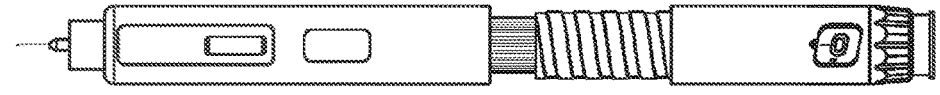
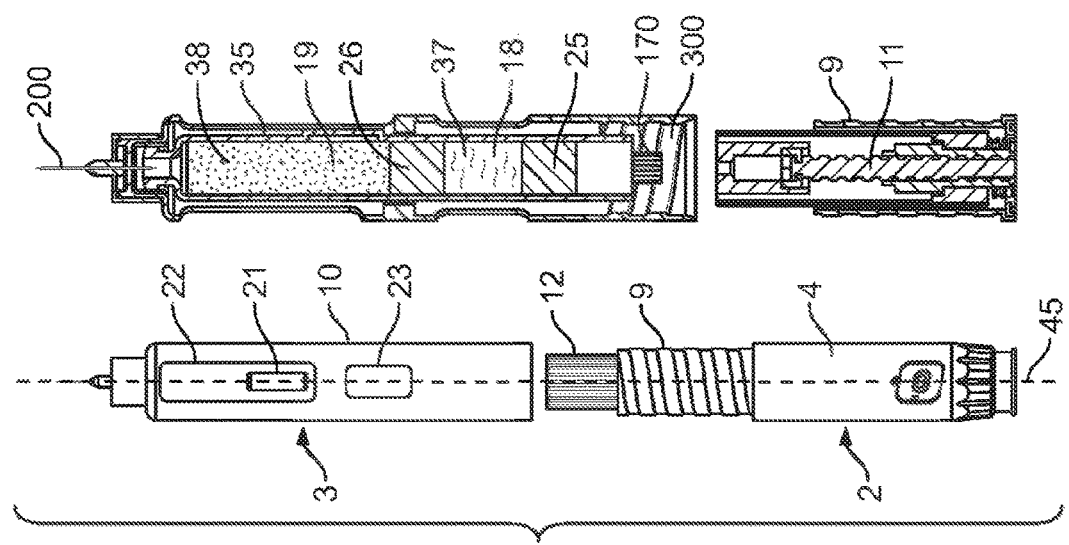

FIG. 15B
FIG. 15A
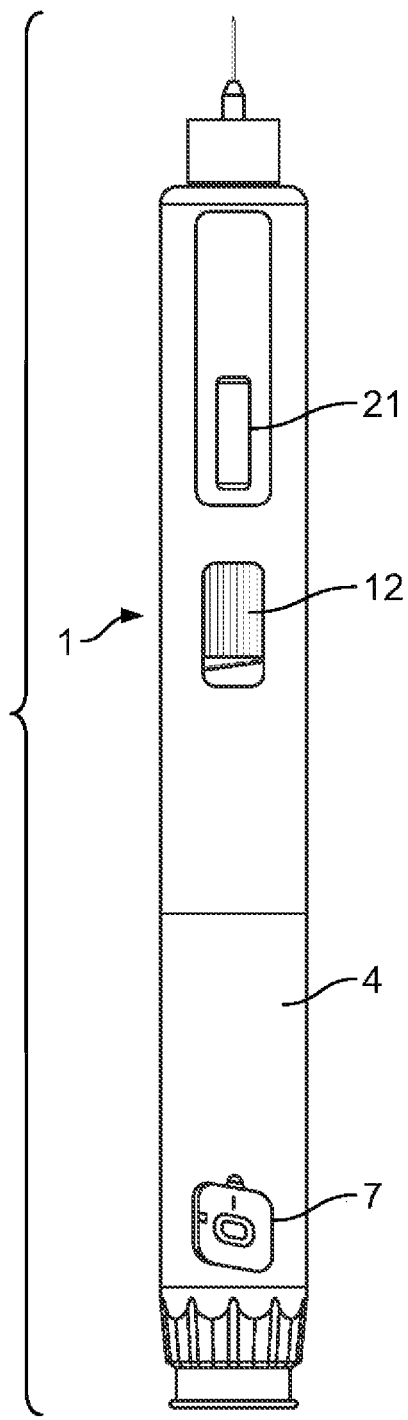
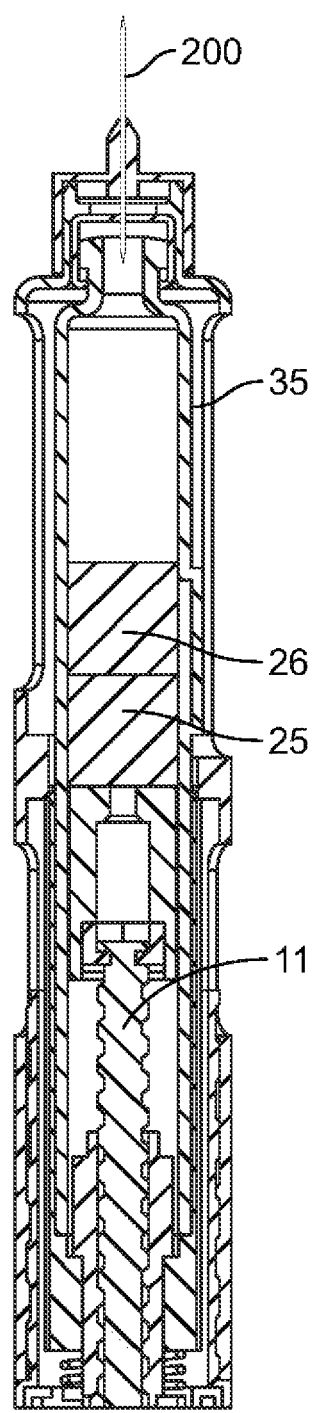

MEDICAMENT DELIVERY DEVICE

CROSS-REFERENCE TO RELATED APPLICATIONS

This application is a divisional of U.S. application Ser. No. 17/021,787, filed Sep. 15, 2020, which is a continuation application of international patent application PCT/EP2019/059150, filed Apr. 10, 2019, designating the United States and claiming priority from U.S. provisional applications 62/657,283, filed Apr. 13, 2018, and 62/688,153, filed Jun. 21, 2018, and the entire content of the above applications is incorporated herein by reference.

BACKGROUND

Field of the Invention

The present disclosure relates to medicament delivery devices, particularly to devices for injecting, administering, infusing, dispensing or delivering a substance, and to methods of making and using such devices. More particularly, it relates to delivery devices for administering a liquid agent, e.g., a medicinal or therapeutic substance or product, from a multi-chamber cartridge or ampoule. e.g. a two-chamber cartridge, multi-chamber container or reservoir, multi-chamber ampoule, etc.

Background of the Invention

There are a number of medicament delivery devices on the market that are capable of automatically, semi-automatically or manually delivering doses of medicament. Of the known type of delivery devices, the "pen-type" injector is popular and is available in both reusable and disposable designs. Such devices are constructed with dose setting mechanisms that include a variety of inter-acting mechanical components to achieve desired functions, such as setting a dose, dose cancellation, and ultimately delivering the set dose. Such devices are typically designed for non-medically trained individuals to self-administer medicaments.

In some cases, users of these medicament delivery devices need to inject medicaments that must be reconstituted with a solvent or diluent before injection. To that end, the injection device must be able to accept cartridges that have two or more chambers, for example, one chamber to hold a lyophilized drug product and another chamber to hold the reconstitution solvent. The contents of the two chambers must be mixed before the injection can occur.

Some of the conventional pharmaceutical products that would undergo lyophilization include bulk pharmaceutical/biopharmaceutical ingredient (chemical or biologics found in nature), protein, collagen, peptide, oligonucleotide, chemical API, enzymes, and mAbs. Lyophilization is typically necessary when the bulk drug ingredients are not stable in liquid or frozen form. This can be due to chemical reactions, degradation, aggregation, biological growth, heat sensitivity, etc. Lyophilization enables longer shelf life, often as long as two-five years and makes it much easier to transport the product. In addition, products can be stored at room temperature. One such example is growth hormone, which cannot be stored for any length of time when dissolved in a liquid. However, to provide successful treatment for growth hormone problems, it is typically necessary to introduce such agents into a patient's body tissue in liquid form.

The separate chambers in multi-chambered cartridges are usually separated from one another by displaceable or slidable stoppers (i.e., pistons). The first or front chamber usually comprises an outlet of the cartridge that sealed by a pierceable membrane (e.g., a septum), the inner cartridge wall and the proximal end face of the first stopper. The second or rear chamber usually is located distally from the first chamber and is formed by the distal end face of the first stopper, the inner cartridge wall and a second stopper. Along the longitudinal axis of the cartridge and hence along the axis along which the stoppers can be pushed and slid, a bypass is disposed in the cartridge wall, which can be used as a fluid bypass for the solvent or dissolving liquid to flow around the first stopper and into the first chamber. To mix the drug agent with the dissolving liquid, a pressure is applied to the second stopper inside the cartridge, where such pressure is transmitted to the first stopper by the non-compressible dissolving liquid. Once a cannula is introduced into the cartridge through the pierceable membrane, the two stoppers can then be pushed or moved along the longitudinal axis of the cartridge relative to the inner wall of the cartridge.

As soon as the first stopper has moved so that it lies adjacent to the region of the bypass, the dissolving liquid passes out of the second chamber through the bypass and flows into the first chamber containing the drug agent. The second stopper can be pushed relative to the inner wall and toward the first stopper until it lies adjacent and preferably touching the first stopper. At this point all of the solvent has been transferred into the first chamber and the second chamber no longer exists. At this point, a cannula, for example a double-ended pen needle, can be attached to the cartridge holder such the cannula pierces the membrane to establish a fluid connection with the first chamber. Now, when the second stopper is pushed again via a piston rod operatively associated with a dose setting mechanism, the first stopper is also moved. Movement of the two stoppers in the proximal direction eventually causes the reconstituted liquid drug in the first chamber to be dispensed through the cannula. When mixing the drug agent with the dissolving liquid, care must be taken to ensure that the agent is not exposed to excessive flows of the dissolving liquid. Foaming should be avoided during mixing before administering an agent in liquid form into a patient's tissue and it is typically to vent the cannula that is in fluid communication with the first chamber.

SUMMARY

It has been determined that although conventional devices may enable the mixing of a solvent with a drug agent, many delivery device designs do not allow the drug agent to be mixed slowly to avoid foaming or prevent damage to the agent. Additionally, users of these types of devices can find it difficult to tell when the mixing procedure is complete, and the drug agent has therefore been fully dissolved in the dissolving liquid in the desired concentration. This can be especially important when multiple injections from a single cartridge are needed. Also, conventional device designs involve the use of a threaded connection between cartridge container and pen injector, which is significantly longer than that of other pen injectors. In such circumstances, it can be difficult to manufacture such a long thread on the delivery device pen injector. Furthermore, in some designs the injectors have a piston rod return features in the form of a rotating ring. This piston rod return ring is manipulated by the user to reset or bring the piston rod back to the rearmost proximal position within the dose setting mechanism. When such a long thread is needed, the piston return ring is no longer accessible.

From the above-noted issues with existing devices, there is a need to have a multi-chamber cartridge medicament delivery device that allows a non-medically trained user to easily operate the device to perform a reconstitution process to result in a liquid medicament formulation immediately prior to the delivery of a set dose of the medicament. The disclosure presented below achieves the above-mentioned goals by providing a robust and relatively easy to use reconstitution delivery device.

This disclosure is directed to drug delivery devices that accept multi-chambered cartridges. These devices are sometimes referred to reconstitution drug delivery devices. Such devices can be designed to allow a user to set multiple and varying single doses until all the medicament in the cartridge is expelled. Alternatively, the dose setting mechanism can be designed to only deliver one or more fixed (non-user settable) doses. In some configurations these devices are known as pen-type injectors.

In one possible embodiment of the present disclosure a medicament delivery device or more specifically a two-piece pen-type injector is described comprising a distal part and a proximal part for delivery of a medicament mixed within a multi-chambered cartridge, where a distal part comprises a dose setting mechanism having a housing, a dose setting knob, an injection button, a piston rod capable of moving axially along the longitudinal axis of the housing during dose delivery, and a return ring configured to reset the piston rod to a starting position. A proximal part comprises a cartridge holder configured to accept a multi-chambered cartridge, where the cartridge holder comprises a screw driven sleeve configured for attachment to the distal part and where rotation of the screw driven sleeve performs a medicament mixing process within the multi-chambered cartridge.

As will be explained in more detail below, the screw driven sleeve can be threaded and configured to cooperate with a threaded portion of distal part. The screw driven sleeve can also have a start position where the screw driven sleeve extends distally from a distal portion of the cartridge holder and have an end position where the screw driven sleeve is retracted proximally into a distal portion of the cartridge holder. Additionally, the screw driven sleeve could also have a snap arm located on an outside surface.

The cartridge holder is configured and designed to accept a multi-chambered cartridge. In some cases, it is desirable to color code the cartridge holder to highlight or distinguish between different medicaments or strengths of a medicament. The cartridge holder can have multiple cut-outs or windows that allows a user to view the contents of the cartridge, including the movement of the slidable stoppers during the reconstitution process. When a two-chambered cartridge is positioned in the cartridge holder a first cut-out can be used to view the second chamber of the cartridge and a second cut-out or window can be used to view the first or most proximal chamber of the cartridge. This second window can also have a narrowed or constricted section that accepts the bypass of the cartridge to hold the cartridge in place in a snap-in notch. The cartridge holder can also be designed and configured to permanently accept a cartridge, i.e., where once the cartridge is inserted into the cartridge holder it cannot be removed unless the cartridge holder is broken or otherwise destroyed. Alternatively, the cartridge holder can be designed and configured to releasably accept a cartridge, such that a user can remove an empty cartridge and replace it with a new, full cartridge. In this design, the cartridge holder need not require a snap fitting notch to secure the cartridge in place.

The first chamber of the cartridge will typically contain a freeze dried or lyophilized drug agent and the second chamber will contain the liquid solvent. The cartridge bypass feature is preferably visible through the second window. The progress of the lyophilization, i.e., the reconstitution process, can be viewed in both windows. In one embodiment of the present disclosure, a user can view through the first window the movement of the return ring as the cartridge holder is being screwed onto the proximal end of the dose setting mechanism. In all embodiments, the second window will allow viewing of the first and/or second stoppers during the reconstitution process.

In one embodiment of the device disclosed, the screw driven sleeve can be designed as a reusable part or as a disposable part. In both cases the sleeve has a first or starting position where it extends distally from the distal end of the distal portion of the cartridge holder. When the screw driven sleeve is designed as disposable, then the cartridge holder and the cartridge are also disposable so the assembly is discarded as a unit once removed from the dose setting mechanism which is reused with a new cartridge holder, sleeve and cartridge assembly. Alternatively, the cartridge holder and the screw driven sleeve can be designed and configured such that only the empty cartridge is removed and discarded, and a new, full cartridge is inserted into the cartridge holder and the sleeve is again attached to the dose setting mechanism. In a third possible embodiment, the sleeve is reusable and removable from the cartridge holder such that the cartridge and cartridge holder are discarded after use. A new cartridge holder and cartridge assembly would be attached to the reusable sleeve. In each possible sleeve design, the distal portion of the cartridge holder has two cut-outs or snap windows, one at the distal end and one at the proximal end. These snap windows are configured to interact with a flexible or snap arm located on the outside of the proximal end of the screw driven sleeve.

The snap arm on the screw driven sleeve can have an outward radially extending protrusion designed to engage each of the snap windows. When the screw driven sleeve is in the first position, the snap arm is releasably engaged with the distal snap window and when the reconstitution process is complete, the screw driven sleeve is fully positioned inside the distal portion of the cartridge holder and the snap arm is engaged with the proximal snap window. In the design where the assembly of the cartridge holder, cartridge and sleeve are all disposable, the engagement of the protrusion with the proximal snap window is non-releasable, i.e., permanent, such that the sleeve cannot be rotated relative to the distal portion of the cartridge holder. In the case where the sleeve is reusable, the protrusion and proximal snap window form a releasable engagement such that an applied rotation torque will disengage the protrusion from the proximal snap window and allow the sleeve to be rotated relative to the cartridge holder. The snap arm is designed such that the protrusion will fit into the proximal snap window when the screw driven sleeve is moved axially inside the cartridge holder and becomes aligned with a snap window. As the screw driven sleeve moves relative to the inside surface of cartridge holder, the protrusion and snap arm are biased radially inward. When the protrusion becomes aligned with a snap window, the snap arm is free to flex radially outward so that the protrusion engages or snaps into the window.

The outside surface of the screw driven sleeve can have a helical or outer screw thread that can engage and cooperate with a like thread located on the inside of the distal portion of the cartridge holder. The outer thread can be a male thread or a female thread. In the latter case, the inside of the distal portion of the cartridge holder could have one more nibs that engage with the female thread as opposed to having a full set of male threads. On the inside distal end of the screw driven sleeve is a fastener that cooperates with a like fastener on the dose setting mechanism. The cooperation of these fasteners allows the distal and proximal parts of the medicament delivery device to be releasably or permanently connected to each other. When a permanent connection is desired the fasteners could cooperate to form an irreversible snap fit. Alternatively, the permanent joint or connection formed by the fasteners could be welded or glued to result in a permanent connection between the dose setting mechanism and the screw driven sleeve such the delivery device would have to be physically broken in order to separate these parts.

In another embodiment, the presently disclosed device is configured such that the reconstitution process requires that the piston rod return ring be rotated so as to move the piston rod axially in the proximal direction as the cartridge holder/cartridge assembly is connected to the dose setting mechanism. In the case where the injection device is reusable, then before the assembly is attached to the dose setting mechanism, the piston rod has to be retracted to the rearmost or start position by rotating a piston rod return ring counter clockwise relative to the dose setting mechanism. In the case of a completely disposable device, there would be no need to retract the piston rod and therefore the device would not need to have piston rod return ring. Because the return ring is rotatably fixed with the piston rod, rotation of the return ring causes the piston rod to rotate. A threaded connection between the piston rod and an internal stationary nut in the dose setting mechanism causes the piston rod to axially move distal or retract back into the dose setting mechanism. Likewise, when the piston rod return ring is turned in a clockwise direction relative to the dose setting mechanism, the piston rod will move axially in the proximal direction, i.e., extend out and away from the dose setting mechanism. The present device is configured such that as the cartridge holder is screwed onto or into the dose setting mechanism by turning it clockwise relative to the dose setting mechanism in a customary and normal procedure, such rotation also rotates the return ring in the same clockwise direction. This results in the piston rod and the distal most stopper in the cartridge moving axially relative to each other as the cartridge holder is attached to the dose setting mechanism. The simultaneous rotation of the return ring and cartridge holder relative to the dose setting mechanism allows the length of the thread on the pen injector to be much less than a conventional reconstitution injection device because of the simultaneous axial movement of the piston rod and cartridge holder in opposite directions as a result of the cartridge holder rotating the return ring.

Preferably an interior portion of the distal end of the cartridge holder is threaded with a screw thread that matches and cooperates with an external threaded proximal end of the dose setting mechanism. The interior distal portion of the cartridge holder can also contain one or more guide elements that can rotational engage the return ring when the proximal part (i.e., the cartridge holder) and the distal part (i.e., the dose setting mechanism) are axially aligned with each other immediately before the two parts are screwed together. The engagement of the guide element with the return ring allows the return ring to be rotated as the cartridge holder is screwed into or onto the dose setting mechanism. Preferably a splined engagement is used between the guide element and the outside surface of the return ring. Such an engagement must allow for relative axial movement between the guide element and the return ring as the distal and proximal parts are screwed together. In a preferred configuration two or more guide elements are used, preferably equally spaced around the inside surface of the cartridge holder. The cartridge holder can be designed as a reusable part or as a disposable part. When the cartridge holder is designed as disposable, then the cartridge is also disposable, so the assembly is discarded as a unit once removed from the dose setting mechanism which is reused with a new cartridge holder and cartridge assembly. Alternatively, the cartridge holder can be designed and configured such that only the empty cartridge is removed and discarded, and a new, full cartridge is inserted into the cartridge holder and the assembly is again attached to the dose setting mechanism.

An outside surface of the proximal end of the dose setting mechanism can have a helical or outer screw thread that can engage and cooperate with a like threaded surface located on the inside of the distal portion of the cartridge holder. Of course, the device could also be manufactured such that the threaded surfaces are reversed, i.e., there is a thread on the outside surface of the cartridge holder and a cooperating thread on the inside of the dose setting mechanism. The outer thread on the dose setting mechanism can be a male thread or a female thread. In the latter case, the inside of the distal portion of the cartridge holder could have one more nibs that engage with the female thread as opposed to having a full set of male threads. When a permanent connection is desired between the cartridge holder and the dose setting mechanism, there could be included a non-releasable snap lock fitting that engages when the distal and proximal parts are screwed securely together. Such an irreversible lock will prevent a user from disassembling these parts in the absence of physically braking one or more components of the delivery device in order to separate these parts.

For each embodiment disclosed, the delivery device can be designed and configured as a reusable or a semi-reusable device, where (1) the cartridge, cartridge holder and sleeve assembly can be replaced once the medicament has been expelled and the dose setting mechanism is reused, (2) the sleeve and the dose setting mechanism are reused and the cartridge holder and cartridge are disposed of, or (3) the cartridge holder, sleeve and dose setting mechanism are reusable and only the empty cartridge is removed and discarded, and (4) the entire reconstitution device is disposed of after the medicament in the cartridge is expelled. In the designs where the dose setting mechanism is reusable, then the fastener on the screw driven sleeve and the cooperating fastener on the dose setting mechanism should also be reusable, i.e., releasably cooperating, for example, a screw thread, a Luer-Lok fitting, a bayonet fitting, detent or a combination of these reliable type connectors. Such a releasable connection allows a user to separate the sleeve from the dose setting mechanism without damaging the dose setting mechanism. In order to reuse the dose setting mechanism the piston rod must be retracted back into the dose setting mechanism. This is referred to as a resetting operation.

In another embodiment where the delivery device is designed and configured as a disposable device, a reusable or a semi-reusable device, (1) the cartridge and cartridge holder can be replaced once the medicament has been expelled and the dose setting mechanism is reused, (2) the cartridge holder and dose setting mechanism are reusable and only the empty cartridge is removed and discarded, and (3) the entire reconstitution device is disposed of after the medicament in the cartridge is expelled. In a completely disposable of this device design, there is no need to retract the piston rod after the medicament in the cartridge is expelled because the entire device is thrown away. However, initially when the cartridge holder/cartridge assembly is attached to the dose setting mechanism, the rotation of the cartridge holder as it is screwed into/onto the dose setting mechanism will rotate a piston rod guide as opposed to a piston rod return ring. The function of the piston rod guide in a completely disposable device is similar to the piston rod return ring in that that it is axially fixed to the housing and rotation in a clockwise direction causes the piston rod to move proximally to perform the reconstitution process. Once the cartridge holder is fully attached to the dose setting mechanism the connection becomes fixed, permanent and irreversible, thus preventing a user from disassembling the cartridge holder from the dose setting mechanism without physically breaking or destroying the device.

In the designs where the dose setting mechanism is reusable, then the fastener or threaded connection on the cartridge holder and the cooperating fastener or thread on the dose setting mechanism should also be reusable. Such a releasable connection allows a user to separate the cartridge holder from the dose setting mechanism without damaging the dose setting mechanism. In order to reuse the dose setting mechanism the piston rod must be retracted back into the dose setting mechanism using the return ring described above by turning the return ring in the counter-clockwise direction. Again, as mentioned, this retraction of the piston rod to a start position is referred to as a resetting operation.

In one possible embodiment of the reconstitution delivery device, the following procedure can be followed. With the cartridge positioned in a cartridge holder, the inner thread of the screw driven sleeve is threadedly engaged with the thread located at the proximal end of the dose setting mechanism. The screw driven sleeve is turned until the terminal distal end face of the sleeve abuts and contacts a terminal proximal end face on the housing of the dose setting mechanism such that the sleeve can no longer be rotated relative to the housing. As mentioned, the cartridge is held in place in the proximal portion of the cartridge holder through the snap-in notch that accepts the radially protruding bypass section of the cartridge. Preferably, the reconstitution device is provided to the end user with the cartridge snapped into the cartridge container and the screw driven sleeve snapped into the distal portion of the cartridge holder through engagement of the snap arm with the first snap window. The solvent can be inspected through the first observation window and the lyophilizate can be inspected through the second observation window.

When the two terminal end faces are in abutment, the proximal end of the piston rod will also be abutment with the distal end face of the second stopper in the cartridge. Rotation of the cartridge holder relative to the screw driven sleeve will cause the snap arm to disengage from the first or distal snap window and allow the sleeve to be screwed into the distal portion of the cartridge holder. Because the protrusion of snap arm is engaged into the first snap window of the cartridge holder, a certain torque has to be applied, before the cartridge holder can rotate relative to the sleeve. Once this initial torque has been applied, the torque to turn the cartridge container relative to the sleeve is low due to the large pitch of the threaded connection between the sleeve and the inside of the cartridge holder. Only when the sleeve is fully screwed to the housing of the dose setting mechanism can the cartridge holder start turning relative to the sleeve, which takes the cartridge holder towards the dose setting mechanism and as such starts the reconstitution process. Thus, a first purpose of the snap arm on the sleeve ensures that the cartridge holder only starts to turn relative to the sleeve when the sleeve is fully attached to the dose setting mechanism. The second purpose of the snap arm becomes evident in the designs where the sleeve is disposable. Here the permanent engagement of the snap arm with the proximal snap window ensures that the user cannot disassemble the assembly when the reconstitution process is completed. Thus, rotation of the cartridge holder in a counter-clockwise direction will unscrew the sleeve from the proximal end of the dose setting housing and then the assembly of the cartridge holder, cartridge and sleeve can be disposed of as a single unit.

Once the distal end of the sleeve is fully fastened to the housing of the dose setting mechanism, a cannula can be used to pierce the membrane to form a fluid communication with the first chamber in the cartridge. This fluid communication is necessary to allow the reconstitution process to continue by acting a pressure relief or vent of the first chamber. With the cannula in place, the cartridge holder can then be rotated relative to both the sleeve and the attached dose setting mechanism, the cartridge holder and cartridge are moved together towards the stationary proximal end of the piston rod. This causes the piston rod to exert an axial force in the proximal direction on the second stopper causing it to move proximally relative to the inside wall of the cartridge. Because the liquid solvent in the second chamber is incompressible the force on the second stopper is directly transferred to the first stopper such that both stoppers, and the solvent located between them, each move axially forward (proximally) towards the bypass section of the cartridge. Any excess pressure in the first chamber as a result of this transferred force from the piston rod is relieved through the cannula. Once the first stopper has moved into alignment with the bypass, the solvent can then flow from the second chamber around the first stopper and empty into the first chamber where it contacts the lyophilized drug agent and reconstitution begins. The pressure of the solvent from the moving second stopper is reduced as the liquid solvent flows through the bypass.

As the cartridge holder continues to rotate and move relative to the screw driven sleeve, the cartridge continues to move relative to the stationary piston rod, thus pushing the second stopper axially in a proximal direction inside the cartridge until all the solvent is forced out of the second chamber and into the first chamber. The two stoppers eventually abut and contact each other and continue to move together proximally relative to the inside wall of the cartridge. When the stoppers abut, the second chamber ceases to exist. When the cartridge holder is fully screwed onto the screw driven sleeve the snap arm becomes aligned with the proximal snap window and the protrusion engages into the snap window securing the screw driven sleeve axially in place. As mentioned, this engagement of the snap arm with the proximal snap window can be permanent, thus irreversibly locking the sleeve to the cartridge holder, or in the case of reusable sleeve, this engagement can be releasable. In either event, once the reconstitution process is complete, the proximal face of the second stopper is now abutting the distal face of the first stopper, essentially acting and functioning as a single stopper to allow for dispensing a set dose as explained below.

The user can now view, inspect and evaluate the reconstituted product through the second observation window. The user then attaches a needle assembly to the proximal end of the proximal portion of the cartridge holder such that a cannula or injection needle pierces the sealing membrane in the cartridge and establishes a fluid communication with the first chamber. At this point the reconstitution delivery device can be primed and then one or move doses can be set and delivered to the user.

In another possible embodiment of the reconstitution delivery device, the following procedure can be followed. With the cartridge positioned within the cartridge holder a cannula can be used to pierce the membrane to form a fluid communication with the first chamber in the cartridge. This fluid communication is necessary for the reconstitution process to continue by acting a pressure relief or vent of the first chamber of the cartridge. This assembly of the cartridge holder, cartridge and cannula, is then axially aligned with the dose setting mechanism having the piston rod retracted to the start position. The assembly is move axially towards the dose setting mechanism until the guide element on the cartridge holder engages with the return ring to form a rotationally fixed, but slidable, connection. The assembly and the dose setting mechanism are moved together until the threads on the two parts engage and the parts can now be screwed together. At this point, preferably the terminal proximal end of the piston rod is abutting the distal facing surface of the second stopper. Further rotation will begin the reconstitution process because rotation of the cartridge holder causes rotation of the return ring which in turn causes the piston rod to move axially in the proximal direction and to engage the distal most piston as further explained below.

The axial proximal movement of the piston rod causes the piston rod to exert an axial force in the proximal direction on the second (distal most) stopper causing it to move proximally relative to the inside wall of the cartridge. Because the liquid solvent in the second chamber is incompressible the force on the second stopper is directly transferred to the first stopper such that both stoppers, and the solvent located between them, each move axially forward (proximally) towards the bypass section of the cartridge. Any excess pressure in the first chamber as a result of this transferred force from the piston rod is relieved through the cannula. Once the first (proximal most) stopper has moved into alignment with the bypass, the solvent can then flow from the second chamber around the first stopper and empty into the first chamber where it contacts the lyophilized drug agent and begins solubilizing the drug agent. The pressure of the solvent from the moving second stopper is reduced as the liquid solvent flows through the bypass.

As the cartridge holder is further rotated and moving axially relative to the dose setting mechanism, the cartridge and piston rod continue to move relative to each other and the piston rod continues pushing the second stopper axially in a proximal direction inside the cartridge until all the solvent is forced out of the second chamber and into the first chamber. The two stoppers eventually abut and contact each other and continue to move together proximally relative to the inside wall of the cartridge. When the stoppers abut, the second chamber ceases to exist. This should occur when the cartridge holder is fully screwed into or onto the dose setting member and the two parts abut each other. Once the reconstitution process is complete, the proximal face of the second stopper is now abutting the distal face of the first stopper, essentially acting and functioning as a single stopper to allow for dispensing a set dose as explained below.

As previously indicated, the user can now view, inspect and evaluate the reconstituted product through the second observation window. At this point the reconstitution delivery device can now be primed and one or more doses can be set and delivered to the user.

A reversible snap fit can be included at the terminal end of the threaded connection between the cartridge holder and the dose setting mechanism so that the two parts will not easily unscrew from each other during use. The reversible snap can be designed such that a user will have to supply a certain amount of rotational torque in order to disconnect the snap fit and allow the cartridge holder/cartridge assembly to rotate in a counter-clockwise direction until it can be removed from the dose setting mechanism.

As mentioned, the cartridge is held in place in the proximal portion of the cartridge holder through the snap-in notch that accepts the radially protruding bypass section of the cartridge. Preferably, the reconstitution device is provided to the end user with the cartridge snapped into the cartridge holder such that the solvent can be inspected through the first observation window and the lyophilizate can be inspected through the second observation window.

These and other aspects of, and advantages with, the present disclosures will become apparent from the following detailed description of the present disclosure and from the accompanying drawings.

BRIEF DESCRIPTION OF DRAWINGS

In the following detailed description of the present disclosure, reference will be made to the accompanying drawings, of which

FIGS. 9A and 9B illustrate several views of a reusable cartridge holder, and

FIGS. 12A-12D illustrate four views of the return ring of the device of FIG. 11;

FIGS. 13A-13C illustrate three views of one possible design of the cartridge holder present disclosure configured for connection to the dose setting mechanism of FIG. 11;

FIGS. 14A-14F illustrate several views of the medicament delivery device of the present invention in three different stages of assembly;

FIGS. 15A and 15B illustrate two views of the complete delivery device after reconstitution in the second or ready-to-inject configuration;

DETAILED DESCRIPTION

In the present application, the term "distal part/end" refers to the part/end of the device, or the parts/ends of the components or members thereof, which in accordance with the use of the device, is located the furthest away from a delivery/injection site of a patient. Correspondingly, the term "proximal part/end" refers to the part/end of the device, or the parts/ends of the members thereof, which in accordance with the use of the device is located closest to the delivery/injection site of the patient.

Figure 2A:
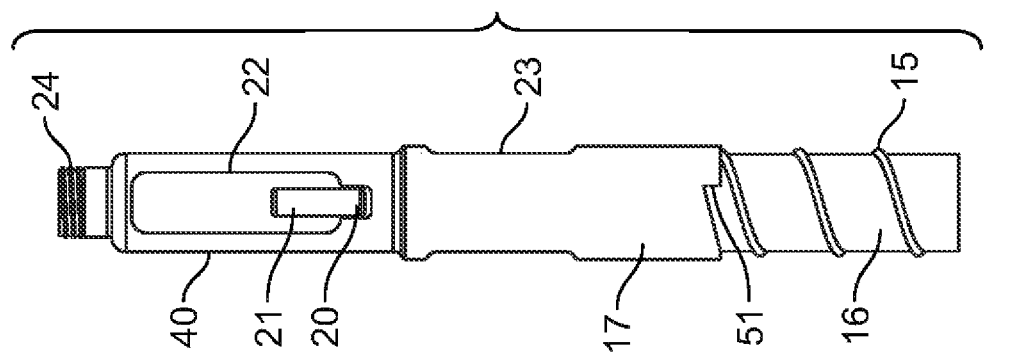
FIGS. 2A and 2B illustrate two views of a possible proximal section of the device of FIG. 1.
Figure 2B:
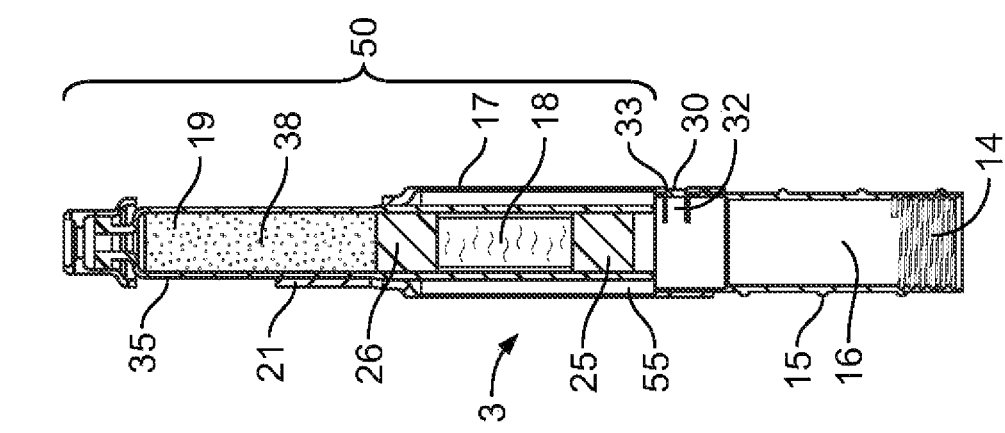
Figure 1:
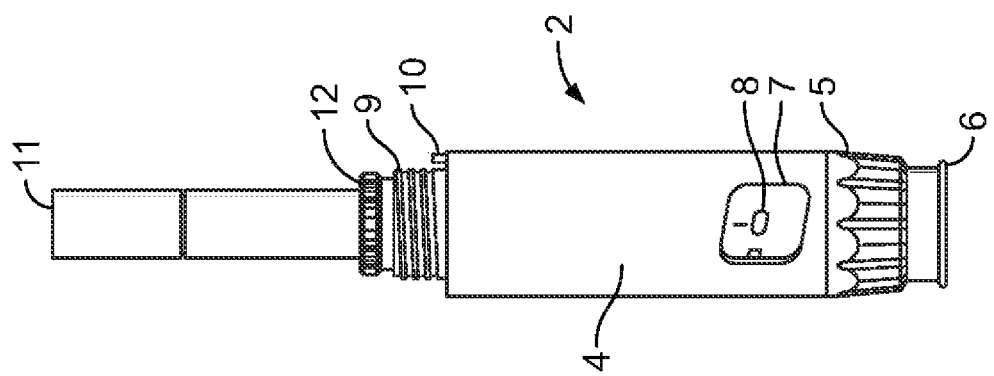
FIG. 1 is an illustration of one possible dose setting mechanism that forms the distal section of one embodiment of the complete reconstitution medicament delivery device of the present disclosure.
Figure 3A:
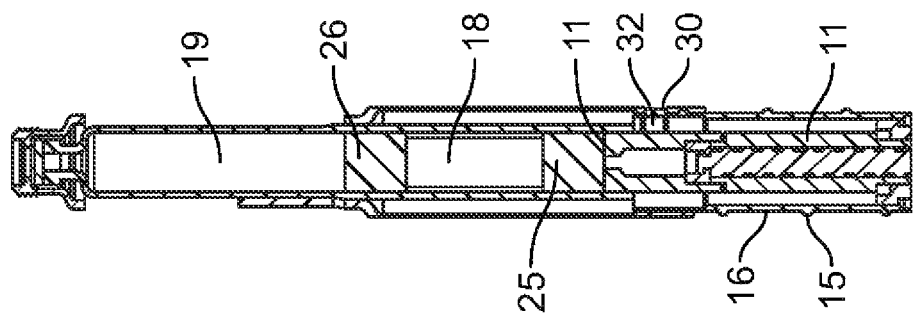
FIGS. 3A-3D illustrate several views of the complete delivery device where the proximal and distal sections of FIGS. 1 and 2A and 2B are connected and the device is in a first or starting configuration.
Figure 3B:
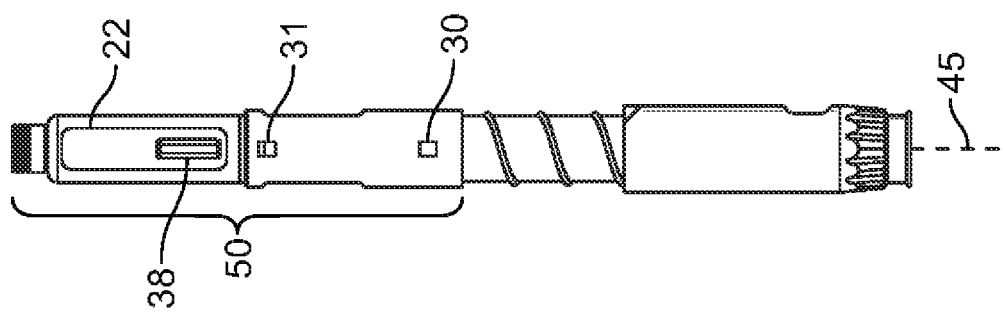
Figure 3C:
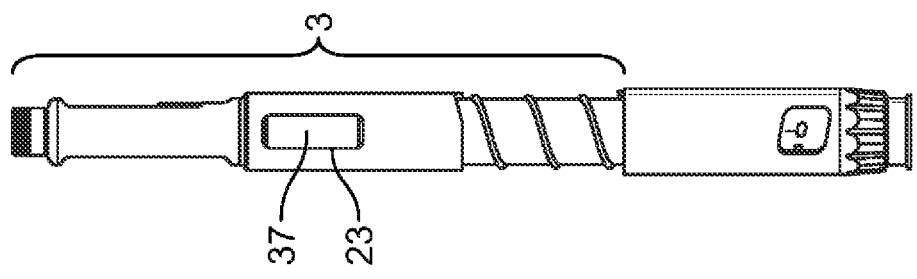
Figure 3D:
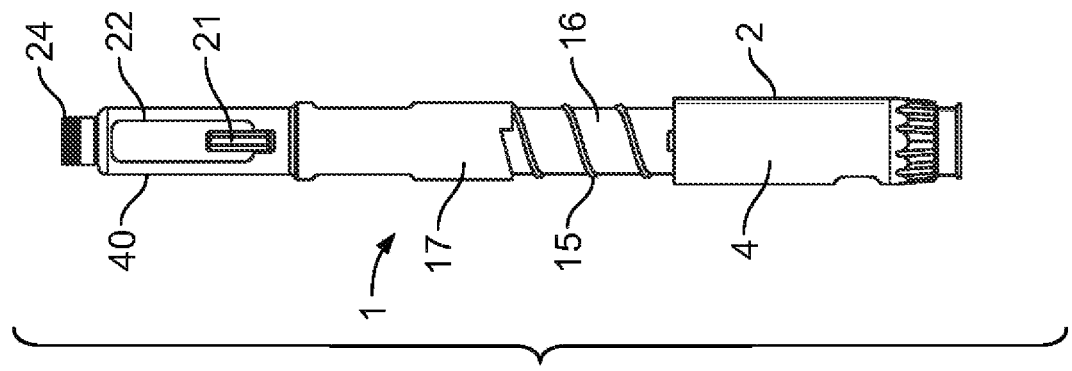

FIGS. 1 and 2A and 2B illustrate the two sections of a semi-disposable device 1 that when connected together (see FIGS. 3A-3D) form one possible complete reconstitution medicament delivery device of the present disclosure. By "semi-disposable" it is meant that the dose setting mechanism is reusable and the cartridge holder and/or the screw driven sleeve is designed and configured to be disposed of along with the empty cartridge after the medicament has been expelled. A "completely disposable" device is one where the sleeve is permanently connected to the dose setting housing and after the reconstitution process the sleeve is also permanently attached to the cartridge holder such that after the expulsion of the medicament, the entire device is disposed of.

The proximal section 2 of device 1 includes the dose setting mechanism. The distal section 3 includes cartridge holder 50 and screw driven sleeve 16, where the cartridge holder includes a distal portion 17 and a proximal portion 40. The dose setting mechanism 2 includes housing 4, piston rod 11, piston return ring 12 (i.e., part of a piston rod reset feature), dose knob 5, button 6, and window 7 to view dose settings 8. At the proximal end of housing 4 is a first thread 9 and may include a radial stop 10 that works to clearly define the radial position of the cartridge holder in the ready-to-use state. The radial stop 10 is designed to interact and abut a cooperating stop 51 on the terminal distal end of distal portion 17 of the cartridge holder when the screw driven sleeve 16 is fully retracted into the cartridge holder and when snap arm 32 engages the proximal snap window 30.

The cartridge holder 50 accepts and securely holds cartridge 35, preferably through a snap fit connection between the bypass 21 and notch 20 located on the second observation window 22 (see FIGS. 2A and 2B). The bypass 21 is part of cartridge 35 and allows the solvent 37 (see FIGS. 5A-5E) to flow from the second or distal chamber 18 into the first or proximal chamber 19 during the reconstitution process where the solvent solubilizes the lyophilized drug agent 38. The lyophilized drug is typically prepared in a lyophilization process that generally involves three stages; freezing, primary drying, and secondary drying. Freezing takes place in a freeze dryer, however, a conventional freezer can also be instead. Freezing temperatures are around −40° C. and there is no thawing before the drying stages. The frozen product goes from frozen state to dry powder through the process of sublimation at reduced pressure to cause the frozen water to sublime directly from the solid phase to the gas phase leaving a dry powder. The solvent used to rehydrate the lyophilized drug agent is typically water or could be any liquid that solubilizes the lyophilized drug and is biocompatible as an injectable material.

The cartridge holder 50 has two observation windows 22, 23. Window 23 can be a cut-out in the distal portion 17 of the cartridge holder. This window 23 allows the user to observe the solvent 37 that is initially contained in chamber 18 when the device is in the starting configuration. As the reconstitution process begins window 23 will show the axial movement of sleeve 16 as it is screwed or retracted into cartridge holder 50. Window 22 is located in the proximal portion 40 of the cartridge holder and can also be a cut-out. Window 22 may also have notch 20 that is designed to engage and secure bypass 21 of the cartridge 35 through, for example, a snap fit connection. This window also allows the user to view the lyophilized drug agent before, during and after the reconstitution process.

The exemplary multi-compartment cartridge 35 (see FIGS. 5A-5E) is shown as a dual chamber cartridge comprised of a first or proximal chamber 19 and a second or distal chamber 18. These chambers are separated by a sliding piston or stopper, namely first stopper 26, the proximal end of chamber 19 is sealed by pierceable membrane or septum 37 that is secured in place by a crimped metal cap 36. The proximal end of cartridge 35 is sealed by a second sliding stopper 25. Solvent 37 is contained between stoppers 25,26. Lyophilizate 38 containing the drug agent is in first chamber 19. FIGS. 5A-5E show the movement and changing chamber configuration during the reconstitution process as the delivery device transforms from the initial or starting configuration (see FIGS. 3A-3D) and progresses to the delivery ready configuration shown in FIGS. 6A-6D. The flow of solvent around the first stopper is also illustrated by arrows 41.

Figure 4B:
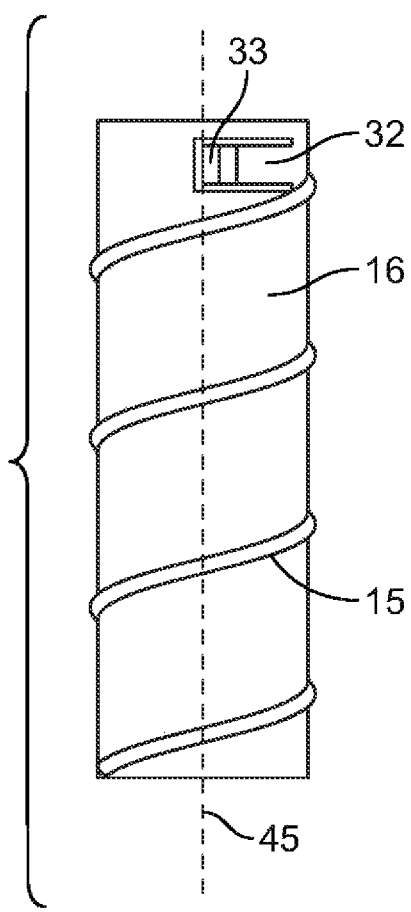
FIGS. 4A and 4B illustrate the screw driven sleeve of the device of FIGS. 3A-3D and a cross-sectional view of same.
Figure 4A:
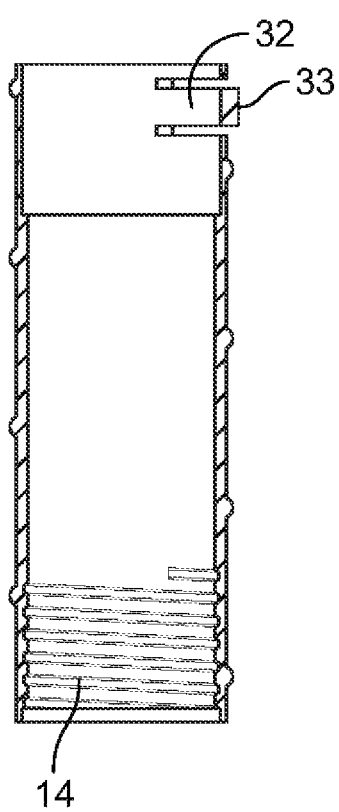
Figure 5A:
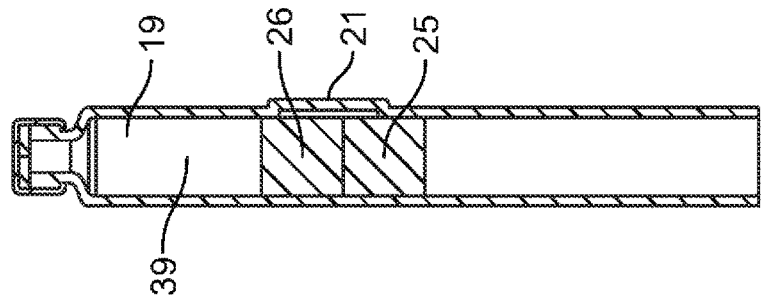
FIGS. 5A-5E show several views of a dual chambered cartridge than can be used in the device of FIGS. 3A-3D.
Figure 5B:
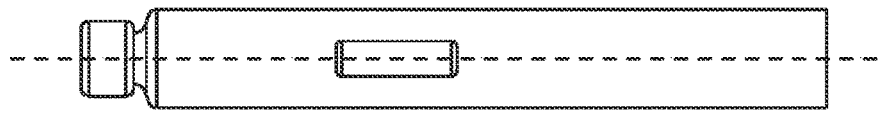
Figure 5C:
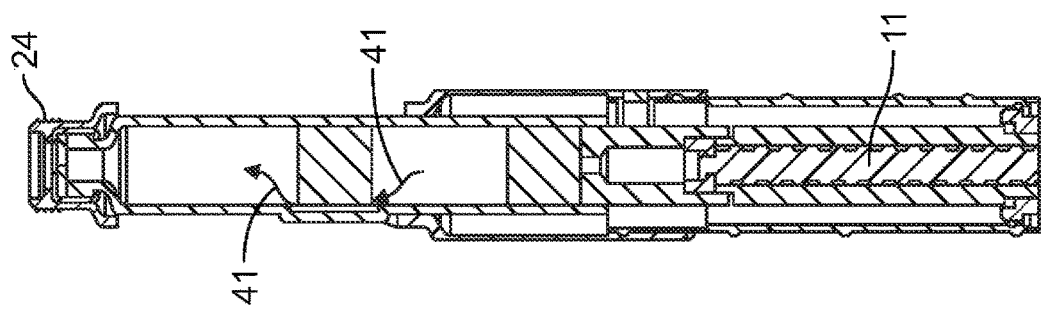
Figure 5D:
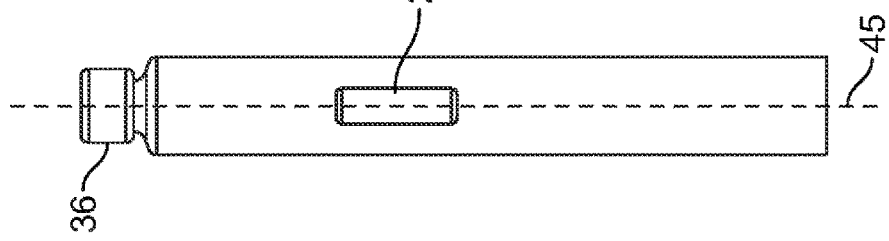
Figure 5E:
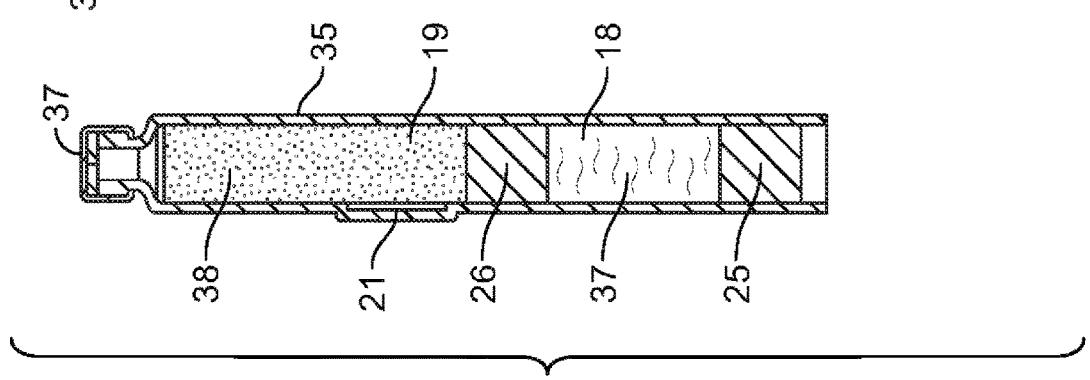
Figure 6A:
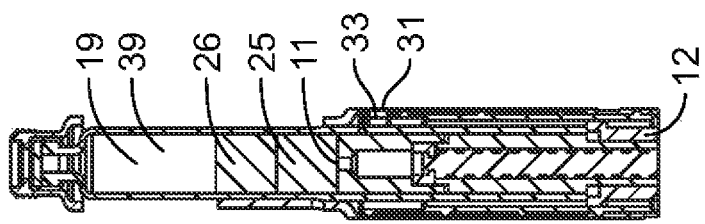
FIGS. 6A-6D illustrate several views of the complete delivery device after reconstitution in second or ready-to-inject configuration.
Figure 6B:
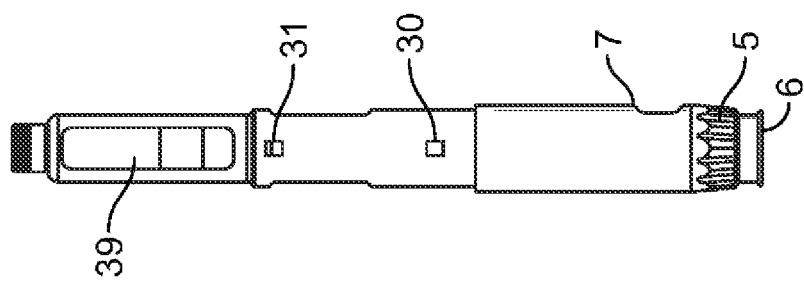
Figure 6C:
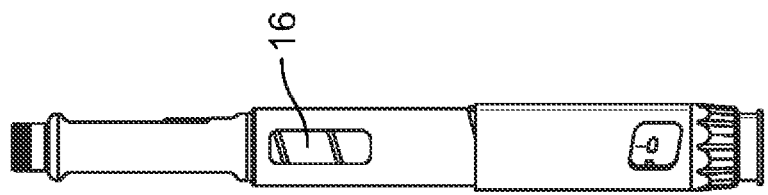
Figure 6D:
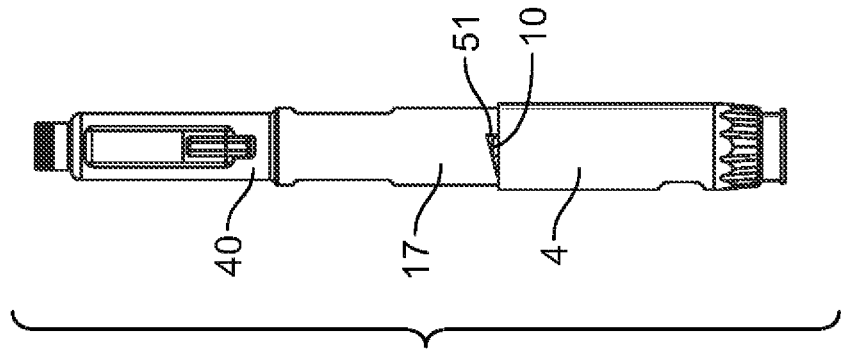
Figure 7A:
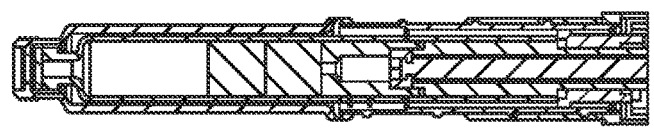
FIGS. 7A-7E illustrate another possible embodiment of the device of the present disclosure where the cartridge holder and screw driven sleeve assembly is reusable.
Figure 7B:
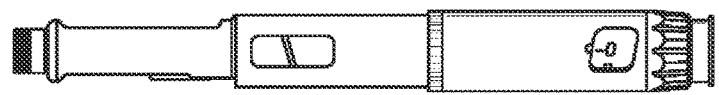
Figure 7C:
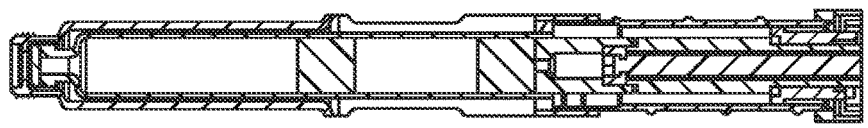
Figure 7D:
Figure 7E:
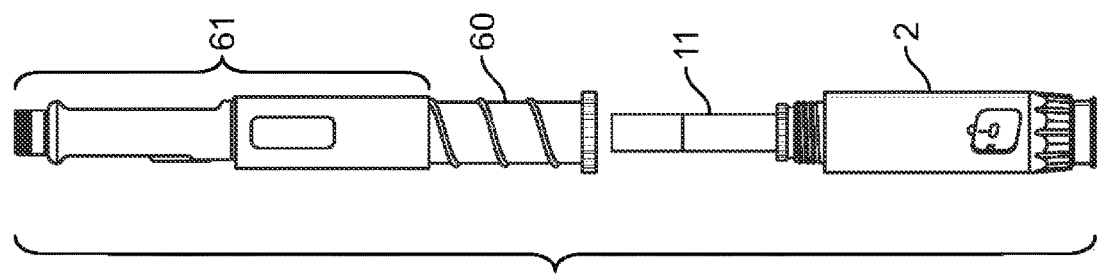
Figures 8A, 8B, 8C:
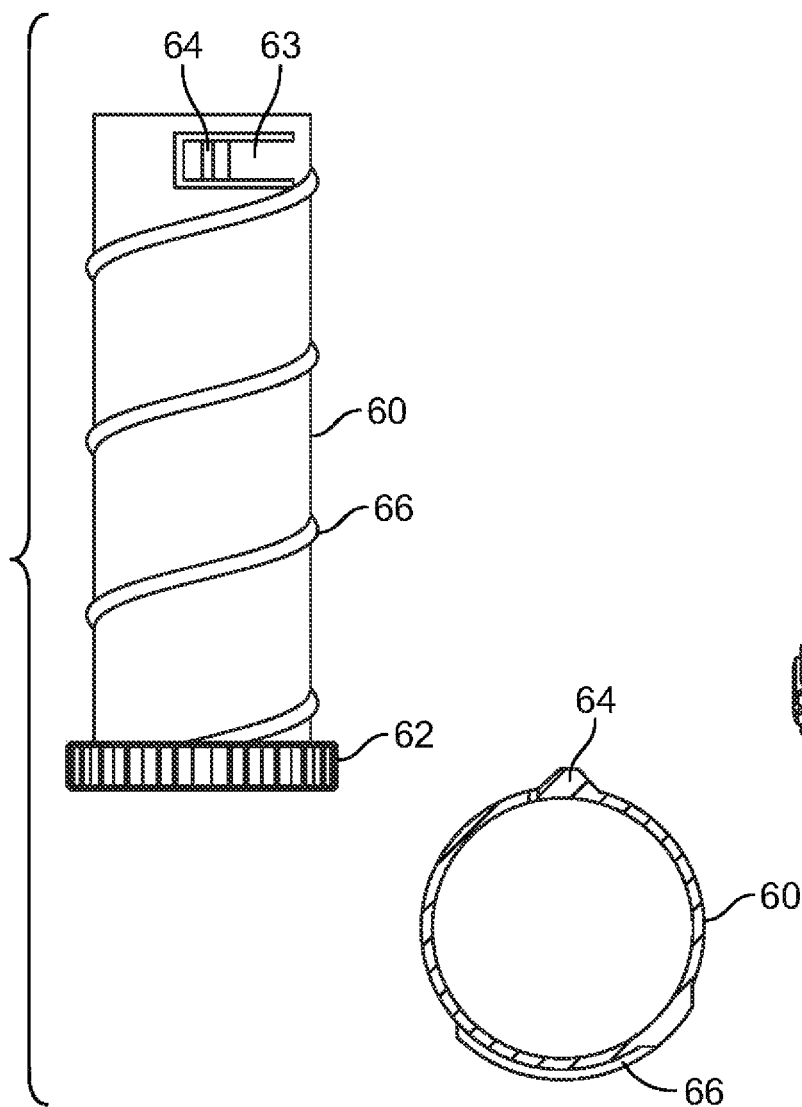
FIGS. 8A-8C illustrate several views of a reusable screw driven sleeve.
Figure 10A:
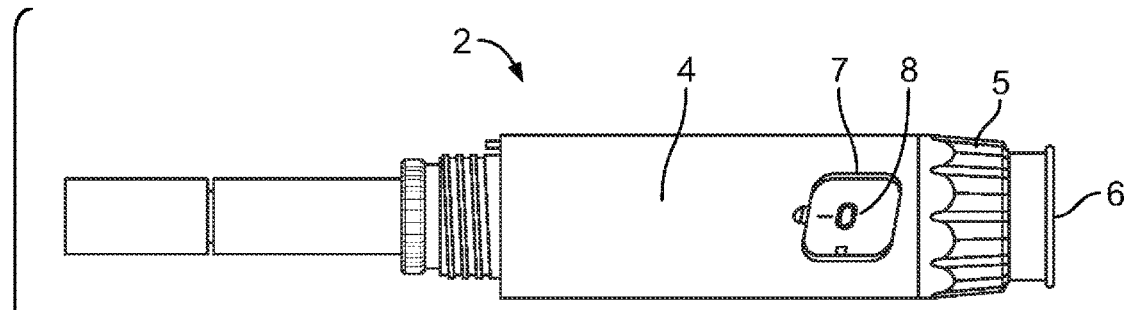
FIGS. 10A-10D illustrate the changing configurations of a possible dose setting mechanism as a user sets and then delivers a dose of medicament.
Figure 10B:
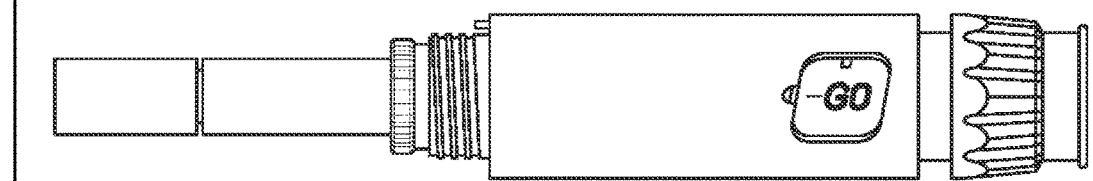
Figure 10C:
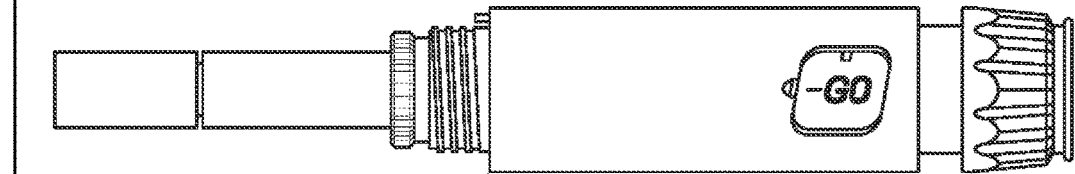
Figure 10D:
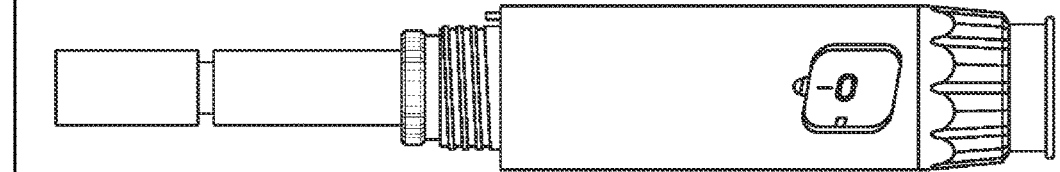

The screw driven sleeve 16 (see FIGS. 4A and 4B) is tube-like cylinder having an internal thread 14 located on the inner proximal surface. The outside surface of sleeve 16 has a thread 15 configured to engage a cooperating thread 55 located inside the distal portion 17 of the cartridge holder (see FIGS. 2A and 2B). In some designs, thread 15 can be a female thread, e.g., a helical groove, that will engage a nib located on the inside surface of distal portion 17. The proximal end of sleeve 16 has at least one flexible or snap arm 32 that has a protrusion 33 that projects radially outward relative to the longitudinal axis 45, which is also the axis of device 1 and cartridge 35. This protrusion is designed to fit into both the proximal and distal snap windows 30,31 that are configured as cut-outs in proximal portion 17 of cartridge holder 50. The flexible snap arm 32 is designed to flex radially inward as the cartridge holder is rotated relative to the screw driven sleeve 16 causing the sleeve to be retracted into the cartridge holder during the reconstitution procedure. Once the cartridge holder has been fully screwed to the sleeve, the protrusion 33 becomes aligned with snap window 31 and the snap arm flexes radially outward such that the protrusion fits into and engages window 31. In the design where the cartridge holder and sleeve are disposable, this engagement is permanent such that a user will not be able to rotate the cartridge holder relative to the sleeve. This permanent locking engagement can be achieved by using an asymmetrically shaped protrusion, sometimes referred to as an irreversible snap lock.

FIGS. 5A-5E shown the position of stoppers 25, 26 relative to bypass 21 after the reconstitution process is complete. As illustrated, chamber 18 is completely subsumed as stopper 25 has moved proximally and in abutment with stopper 26. At this stage the device 1 is now ready to be primed and/or to perform an injection once a needle is attached to connection 24.

The present disclosure is applicable with a number of injection device designs. FIGS. 1 to 6D illustrate just one possible type of pen-shaped injection design as being a semi-disposable device, where the only the dose setting mechanism is designed and configured for reuse. In such a device, after the reconstitution process is complete and after the medicament has been expelled from the cartridge, the user detaches the cartridge holder/screw driven sleeve assembly containing the empty cartridge from the reusable dose setting mechanism and discards the assembly. A new assembly, containing a fresh cartridge, can then be connected to the dose setting mechanism and the reconstitution process/medicament delivery sequence can be repeated. The used cartridge holder/screw driven sleeve assembly is characterized in that the screw driven sleeve is fully contained within (i.e., screwed into) the cartridge holder and no part of it is accessible by the user. Further, because the snap arm is in a permanent connection with the proximal snap window, even if the user tried to turn the screw driven sleeve the permanent connection would prohibit any relative rotational movement between the cartridge holder and screw driven sleeve.

For a device design where the either the cartridge holder or screw driven sleeve or both are to be reused, it is necessary to unscrew the screw driven sleeve from the inside of the cartridge holder. To that end, it is helpful to provide a user assist component. FIGS. 7A to 9B illustrate a device design where the screw driven sleeve and the cartridge holder is to be reused. In order to reuse the screw driven sleeve 60, it is necessary to have a releasable or non-permanent engagement between the snap arm 63 and the proximal snap window such that the cartridge holder 61 can be rotated relative to the screw driven sleeve 60 along thread 66. This will cause the screw driven sleeve 60 to extend outward of the inside of the cartridge holder and return to the starting position. This releasable engagement can be achieved by using a symmetrical protrusion 64 on snap arm 63 (see FIGS. 8A-8C). As explained above, once the medicament delivery is completed, the user will counter rotate the cartridge holder, which will also counter rotate the screw driven sleeve because of the snap fit of the proximal snap window with the protrusion on the snap arm. Once the assembly is disconnected from the reusable dose setting mechanism, the user must be able to counter rotate the screw driven sleeve to reset the sleeve to the starting position where the snap arm is releasably engaged with the distal snap window. One possible design to assist the user in this resetting of the screw driven sleeve is to include a knurled ring 62 on the distal end of the screw driven sleeve. This gripping surface will provide leverage, so the user can exert the needed torque to overcome the snap fit between protrusion 64 and the proximal snap window. Ring 62 could also be used to provide a user leverage to disconnect thread 65 from the dose setting mechanism. Cartridge holder 61 can also have a second or proximal window 69 with a reduced section 68 that allows an empty cartridge to be removed and new, full cartridge 35 to be slid into the cartridge holder 61 (see FIGS. 9A and 9B).

Device 1 has a dose dial sleeve that translates in a longitudinal direction during dose setting, dose correction and dose delivery. A dose is set through rotation of dose knob 5, which causes the dose dial sleeve to move linearly in the distal direction. A dose is delivered by pushing button 6 on the end of the dose knob 5 in the opposite or proximal direction. This in turn causes the dose dial sleeve to move linearly back (proximally) into the dose setting mechanism 2. One exemplary sequence of a possible dose setting mechanism is illustrated in FIGS. 10A-10D, where the dose setting mechanism is shown in the zero-set dose position ("0" on scale 8), when the dose is set, that start of the injection when button 6 is pressed, and the end of injection where the piston rod has moved proximally an axial distance proportional to the set dose of medicament. The dose setting mechanism shown in FIGS. 10A-10D is designed and configured to only allow setting of a fixed, single predetermined dose that is signified by "GO" on scale 8.

The pen-type injector design shown in the figures will now be described with more detail as to the component parts and their operation. The complete injection device 1 is illustrated in the zero-dose state as indicated by scale 8 showing a zero through the window 7 of housing 4 (see FIGS. 7A-7E). FIGS. 3A-3D show the device 1 with a protective cap removed to expose the cartridge holder 50 having a proximal needle connector 24 at the proximal end. A double-ended pen needle is typically attached to the needle connector 24 through a snap fit, thread, Luer-Lok, or other secure attachment with that the double ended needle cannula can achieve fluid communication with reconstituted medicament 39 within chamber 19 of cartridge 35 positioned within cartridge holder 50. The cartridge 35 is sealed at the proximal end by septum 37 (see FIGS. 5A-5E).

As mentioned, the dose setting mechanism can be designed and configured as a fixed dose device. Alternatively, the dose setting mechanism could allow for setting of one or more user selected doses through the rotation of the dose knob 5 relative to housing 4. Part of the dose setting mechanism of most pen-type injectors is a piston rod 11 as illustrated in FIGS. 1, 5A-5E and 10A-10D. Such piston rods usually have a non-circular cross-section and have two flat surfaces that are designed to prevent the piston rod from rotating but allowing it to move linearly in the proximal direction. As the piston rod moves proximally it pushes stoppers 25,26 proximally to expel medicament 39. The piston rod 11 is held in a non-rotational state relative to housing 4 during both dose setting and dose delivery because it is arranged within a non-circular pass through hole in the center of a piston rod guide. The piston rod guide is both rotationally and axially fixed to housing 4. This fixation can be achieved when the piston rod guide is a separate component from the housing 4 or the piston rod guide could be made integral with the housing.

If the device is not pre-primed during the device assembly or does not have an automatic or forced priming feature, then the user will need to manually prime the device as follows. The dose knob 5 is rotated such that an amount of medicament 39 will be expelled from cartridge 35. The injection device 1 of this disclosure can also have a so-called forced or automatic priming feature where prior to using the dose setting mechanism, i.e., before a user could dial a dose, a sliding lock or other mechanism would necessarily need to be activated such that an amount of medicament is expelled.

In some instances, the user may need to cancel the priming procedure or a previously set dose. This achieved through a dose canceling procedure. Dose cancellation is accomplished by turning the dose knob in the opposite direction used to set a dose. During dose cancellation, certain components in the dose setting mechanism rotate and translate axially in the opposite or proximal direction compared to the dose setting procedure.

During dose setting, the dose knob 5 translates out and away from the distal end of housing 4. As the dose dial sleeve rotates and translates distally, the progress of the dose setting (or dose cancellation) is observed in window 7 as printed indicia on the dose dial sleeve moves past the window. When a desired dose setting is reached the indicia 8 for that dose will appear in the window. At this point the injection device 1 is ready for a priming procedure or, if already primed, the delivery of the medicament to an injection site. In either the case, the user will push button 6 on the dose knob in the proximal direction until the zero-dose hard stop is reached and a zero-dose indicia is observed in the window. During a priming step the user will observe whether medicament is expelled out of the cannula of a pen needle. If no medicament is expelled this means the piston rod is not in abutment with the distal face of sliding piston or stopper 25. The priming step is then repeated until medicament is observed exiting the cannula.

The dose setting mechanism of the present disclosure can also have a maximum dose hard stop feature that prevents a user from setting a dose greater than the highest predetermined dose setting.

Once a dose has been dialed on the dose setting mechanism, the user can then exert an axial force in the proximal direction on button 6 to initiate the dose delivery procedure. The axial force exerted by the user overcomes a distally directed force exerted by a biasing member causing the piston rod 11 to move axially in the proximal direction. Axial movement of the piston rod causes the sliding stoppers to also move axially relative to the inside walls of chamber 19 of the stationary cartridge 35 forcing an amount of medicament 39 out of the needle cannula 6 that is equivalent to the dose that was set by the user during the dose setting procedure.

If the device is configured as a disposable injection device, then the cartridge 35 is not replaceable because the connection between the cartridge holder 50 and the housing 4 of the dose setting mechanism 2 is permanent. Only through breaking or deformation of this connection can the cartridge be removed from the injection device. Such a disposable device is designed to be thrown out once the medicament has been expelled from the cartridge.

In an alternate embodiment, FIG. 11 and FIGS. 13A-13C illustrate the two sections of a semi-disposable device 1 that when connected together (see FIGS. 15A and 15B) form another possible complete reconstitution medicament delivery device of the present disclosure. As described above, this embodiment can be designed as a "semi-disposable" or "completely disposable" device.

The distal part of device 1 includes the dose setting mechanism 2. The proximal part 3 includes cartridge holder 50, where the cartridge holder includes a distal portion 50b and a proximal portion 50a. The dose setting mechanism 2 includes housing 4, piston rod 11, piston return ring 12 (i.e., part of a piston rod reset feature), dose knob 5, button 6, and window 7 to view dose settings 8. At the proximal end of housing 4 is a thread 9 and may include a radial stop 9a or snap fit that works to clearly define the radial position of the cartridge holder relative to the dose setting mechanism after the reconstitution procedure when the device is in the ready-to-use state. The radial stop 9a is designed to interact and abut a cooperating stop of snap fit feature on the terminal distal end of distal portion 50b of the cartridge holder when the cartridge holder and dose setting mechanism have been screwed together and abut one another.

FIGS. 12A-12D illustrates a close-up of the return ring 12 removed and separated from the dose setting mechanism 2 for clarity purposes. The outside surface 12a of the return ring can contain a plurality of longitudinal splines 12b. These splines function as a gripping surface for the user to facilitate gripping and rotating the return ring in the counter-clockwise direction (relative to the dose setting mechanism 2) when it becomes necessary to reset (retract) the piston rob back into the dose setting mechanism to a starting position. These splines 12b also function as an engagement surface for one or more guide elements 170 (see FIGS. 13A-13C). The return ring 12 has an inner surface that may be non-circular and having a shape 310 that conforms to the piston rod such that the return ring and the piston rod are axially fixed to each other.

Guide elements 170 can be positioned on the inside surface 50c of cartridge holder 50 and configured with a plurality of longitudinal splines 170a that are designed to cooperate and engage with splines 12b. Guide elements 170 are rotationally fixed to the inside surface 50c of the cartridge holder 50 and can be separate components that are fixedly attached to the inside surface or the guide elements can be fabricated as integral parts of the inside surface, for example, through a molding process. When the cartridge holder and the dose setting mechanism are axially aligned with each other and then brought together, splines 170a and 12b will engage and axially slide relative to each other forming a rotationally fixed engagement such that clockwise rotation of the cartridge holder (relative to the dose setting mechanism) will cause clockwise rotation of the return ring 12. This rotation of the return ring will cause rotation of the piston rod 11, which in turn will cause it to translate axially out of the dose setting mechanism in the proximal direction. The inner surface 12c of the distal end of return ring 12 is configured to engage the piston rod 11 in a rotationally fixed manner, for example, by having a non-circular cross-section 310 as illustrated in FIGS. 12A-12D.

FIGS. 18A-18F present alternative design of the above described interaction between a cartridge holder 100 and a dose setting mechanism (not shown), where both assemblies are fully disposable. In this design, there is no return ring. Instead there is a piston rod guide 150 axially fixed within the dose setting mechanism and having two longitudinally extending fingers 152 projecting proximally from a guide 153 having non-circular inner portion 154 that prevents relative rotation of the piston rod. The fingers 152 are separated by a slit or gap 151 that is designed to slidably accept corresponding radial projections 101 fixedly attached (both axially and rotationally) to the inside surface 102 of cartridge holder 100. The dimension of the gaps 151 and/or projections 101 are selected such that projections 101 fit within the gaps 151 abutting the sides of the fingers 152 when the cartridge holder 100 is aligned with the dose setting mechanism. As the cartridge holder is screwed into/onto the dose setting mechanism, the rotating projections 101 engage the fingers 152 causing the piston rod guide 150 to engage and rotate. Rotation of the piston rod guide 150 also rotates the guide 153 and non-circular portion 154, which engages and rotates the piston rod. This causes the piston rod to translate axially forward in the proximal direction initiating the reconstitution process. Once the cartridge holder 100 has been fully assembled with the dose setting mechanism the piston rod guide 150 is locked rotationally relative to the dose setting mechanism housing and therefore prevents rotation of the piston rod during dose setting and dose delivery.

The cartridge holder 50 accepts and securely holds cartridge 35, preferably through a snap fit connection between the bypass 21 and a notch or other secure connector located on or near the second observation window 22 (see FIGS. 13A-13C). The bypass 21 is part of cartridge 35 and allows the solvent 37 (see FIGS. 16A-16E) to flow from the second or distal chamber 18 into the first or proximal chamber 19 during the reconstitution process where the solvent solubilizes the lyophilized drug agent 38. The lyophilized drug is typically prepared as described above.

The cartridge holder 50 has two observation windows 22, 23 (see FIGS. 18A-18F). Window 23 can be a cut-out in the cartridge holder that allows the user to observe the solvent 37 that is initially contained in chamber 18 when the device is in the starting configuration. As the reconstitution process begins, window 23 will show the axial movement of return ring 12 in the proximal direction as the cartridge holder is screwed onto the dose setting mechanism via the engagement of threads 9 and 300. Window 22 is also located in the cartridge holder 50 and can also be a cut-out. Window 22 may also have notch that is designed to engage and secure bypass 21 of the cartridge 35 through, for example, a snap fit connection. This window 22 also enables the user to view the lyophilized drug agent before, during and after the reconstitution process.

The exemplary multi-compartment cartridge 35 (see FIGS. 16A-16E) is shown as a dual chamber cartridge comprised of a first or proximal chamber 19 and a second or distal chamber 18. These chambers are separated by a sliding piston or stopper, namely first stopper 26, the proximal end of chamber 19 is sealed by pierceable membrane or septum 37 that is secured in place by a crimped metal cap 36. The proximal end of cartridge 35 is sealed by a second sliding stopper 25. Solvent 37 is contained between stoppers 25,26. Lyophilizate 38 containing the drug agent is in first chamber 19. FIGS. 16A-16E show the movement and changing chamber configuration during the reconstitution process as the delivery device transforms from the initial or starting configuration (see FIGS. 14A-14F) and progresses to the delivery ready configuration, the right-hand illustration in FIGS. 16A-16E. The flow of solvent around the first stopper is also illustrated by arrows 41.

Figure 11:
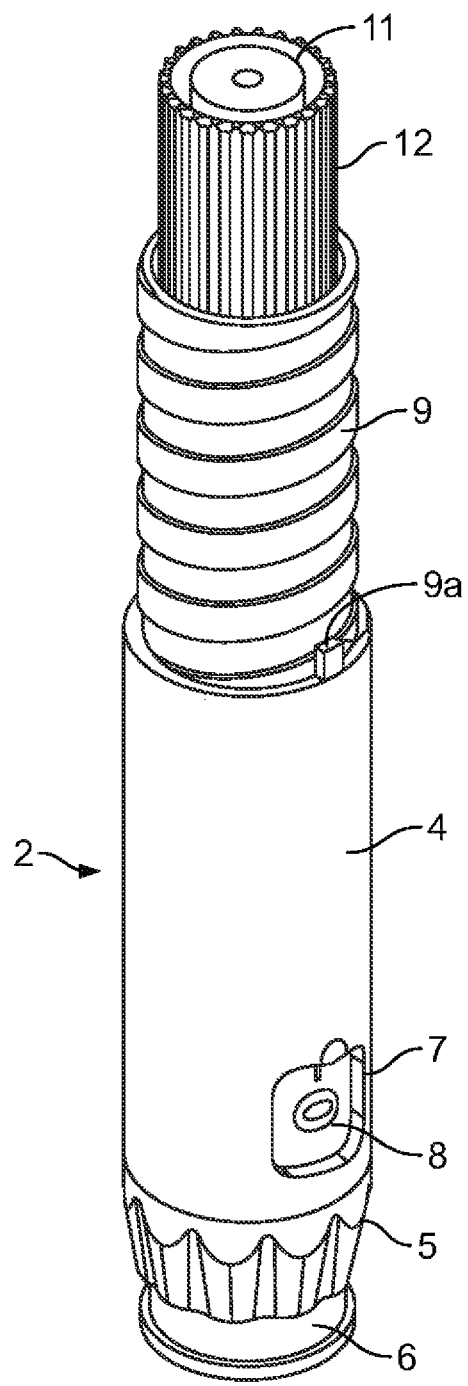
FIG. 11 is an illustration of one possible dose setting mechanism that forms the distal section of one embodiment of the complete reconstitution medicament delivery device of the present disclosure.
Figure 16A:
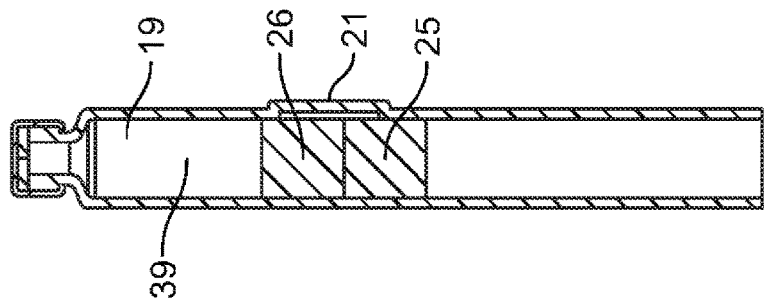
FIGS. 16A-16E show several views of a dual chambered cartridge than can be used in the cartridge holder of FIG. 13.
Figure 16B:
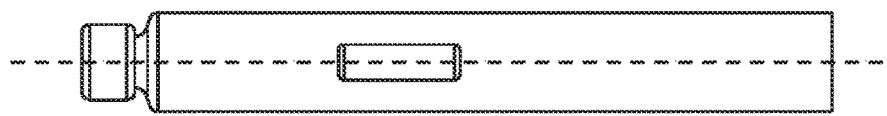
Figure 16C:
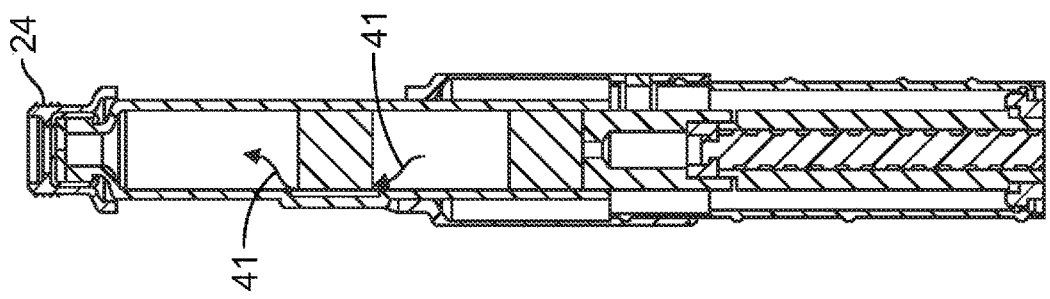
Figure 16D:
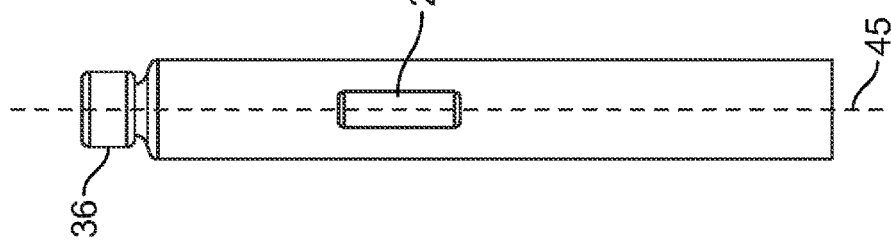
Figure 16E:
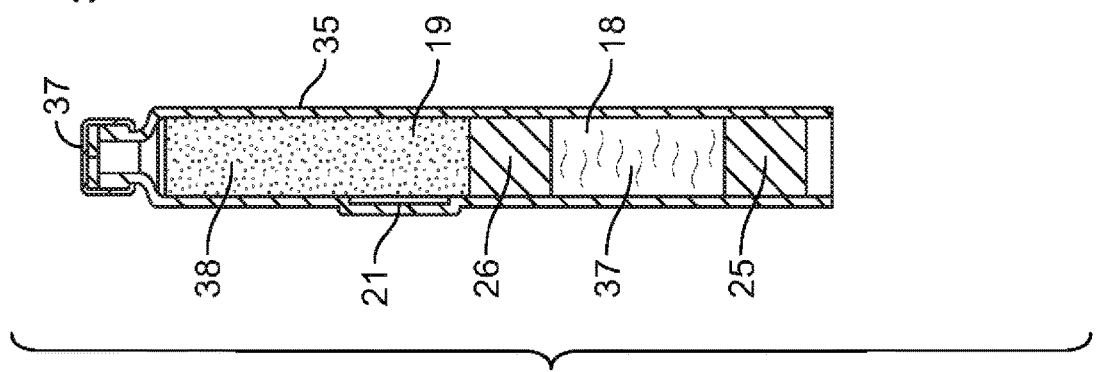
Figure 17A:
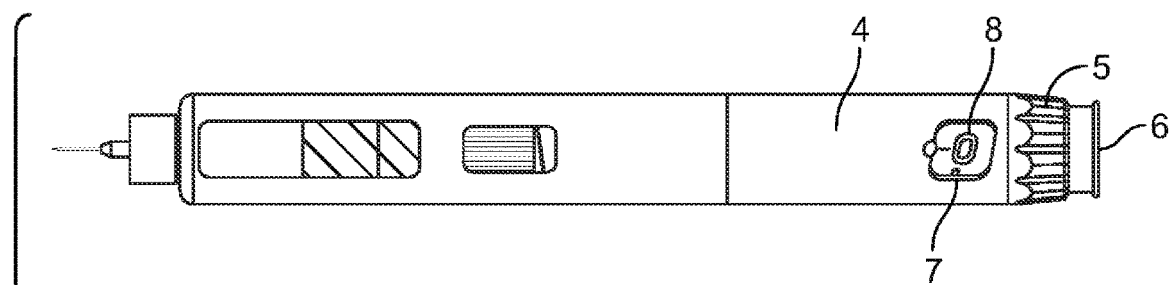
FIGS. 17A-17C illustrate a sequence of a possible dose setting mechanism for the dose setting mechanism of FIG. 11.
Figure 17B:
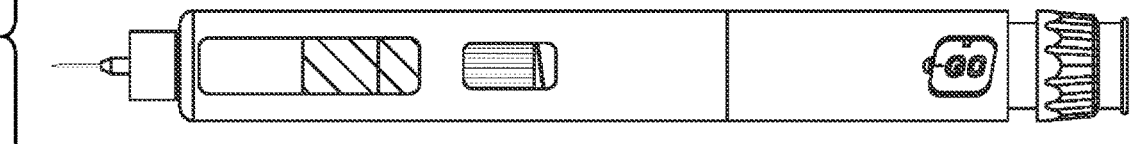
Figure 17C:
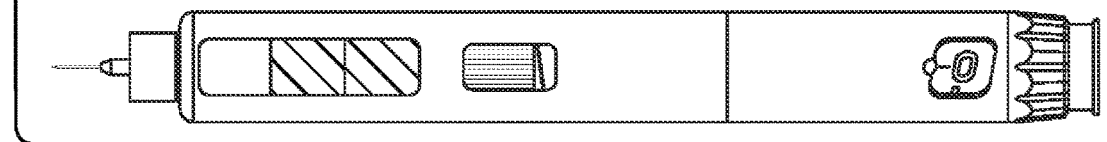
Figure 18D:
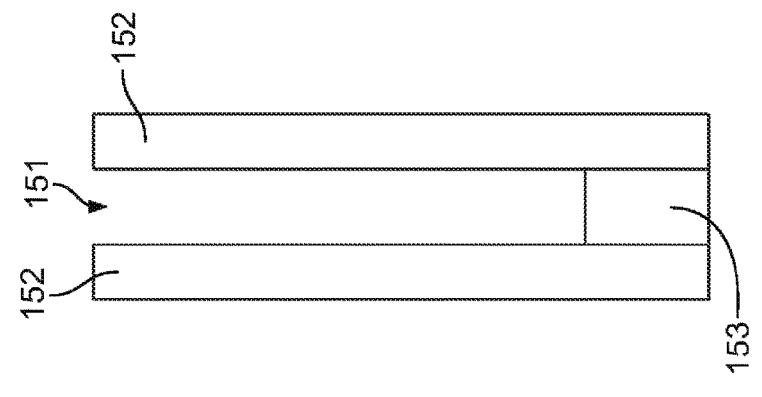
FIGS. 18A-18F illustrate several view of an alternative fully disposable design of the cartridge holder of the present disclosure configured for connection to a disposable dose setting mechanism.
Figure 18F:
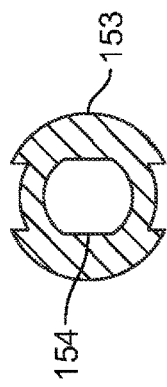
Figure 18C:
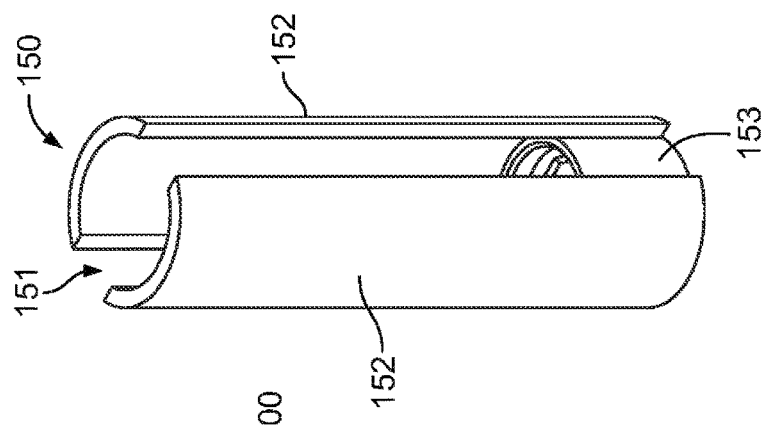
Figure 18B:
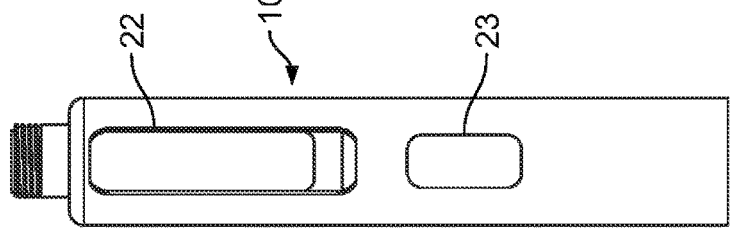
Figure 18A:
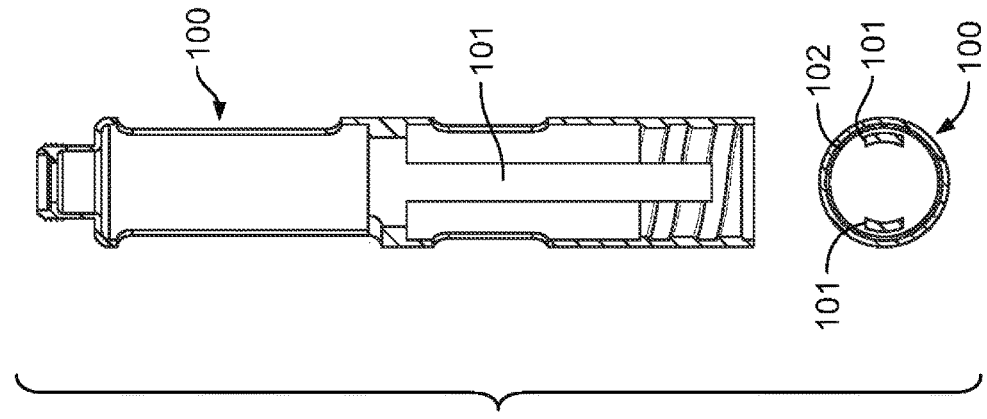
Figure 18E:
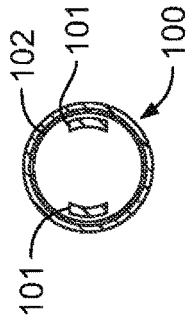

FIG. 11 shows the threaded tube-like cylinder having external threads 9 located on an outer proximal surface of the dose setting mechanism 2. This threaded outside surface is configured to engage a cooperating thread 300 located inside the distal portion of the cartridge holder (see FIGS. 13A-13C). In some designs, thread 300 can be a female thread, e.g., a helical groove, that will engage a nib located on the inside surface of distal portion 17. A radial stop or snap feature 9a can be included on thread 300 such that when the cartridge holder has been fully screwed onto the dose setting mechanism the hard stop or snap feature will engage a corresponding feature on the inside surface of the cartridge holder to provide a tactile feedback to the user that the two parts are securely connected. In a design where the delivery device is completely disposable, this engagement is permanent such that a user will not be able to reverse the rotation of the cartridge holder relative to the dose setting sleeve. This permanent locking engagement can be achieved by using an asymmetrically shaped protrusion, sometimes referred to as an irreversible snap lock.

FIGS. 15A and 15B show the position of stoppers 25, 26 relative to bypass 21 after the reconstitution process is complete. As illustrated, chamber 18 is completely subsumed as stopper 25 has moved proximally and in abutment with stopper 26. At this stage the device 1 is now ready to be primed and/or to perform an injection once a needle 200 is attached to connection 24.

As with the embodiments described above, this embodiment is applicable with a number of injection device designs. The pen-type injection device of FIGS. 11 to 16E is just one possible design of an injection device, one that is either completely reusable or a semi-disposable device, where after the reconstitution process is complete and after the medicament has been expelled from the cartridge through one more injections, the user detaches the cartridge holder containing the empty cartridge from the reusable dose setting mechanism and discards the assembly. A new assembly, containing a fresh cartridge, can then be connected to the reusable dose setting mechanism and the reconstitution process/medicament delivery sequence can be repeated. Alternatively, the device could be completely reusable, where the cartridge holder is designed for reuse as well and where the empty used cartridge is removed and replaced with a full cartridge.

Device 1 has a dose dial sleeve that translates in a longitudinal direction during dose setting, dose correction mid dose delivery. A dose is set through rotation of dose knob 5, which causes the dose dial sleeve to move linearly in the distal direction. A dose is delivered by pushing button 6 on the end of the dose knob 5 in the opposite or proximal direction. This in turn causes the dose dial sleeve to move linearly back (proximally) into the dose setting mechanism 2. One exemplary sequence of a possible dose setting mechanism is illustrated in 17A-17C, where the dose setting mechanism is shown in the zero-set dose position ("0" on scale 8), when the dose is set, that start of the injection when button 6 is pressed, and the end of injection where the piston rod has moved proximally an axial distance proportional to the set dose of medicament. The dose setting mechanism shown in FIGS. 7A-7E is designed and configured to only allow setting of a fixed predetermined dose that is signified by "GO" on scale 8.

The pen-type injector design shown in FIGS. 11 to 18F will now be described with more detail as to the component parts and their operation. The complete injection device 1 is illustrated in the zero-dose state as indicated by scale 8 showing a zero through the window 7 of housing 4. FIGS. 15A and 15B show the device t with a protective cap removed to expose the cartridge holder 50 having a pen needle 200 connected to a needle connector 24 at the proximal end (see FIGS. 13A-13C). A double-ended pen needle is typically used mounted in a hub and attached to needle connector 24 through a snap fit, thread. Luer-Lok, or other secure attachment with that the double ended needle cannula can achieve fluid communication with reconstituted medicament 39 within chamber 19 of cartridge 35 positioned within cartridge holder 50. The cartridge 35 is sealed at the proximal end by septum 37 (see FIGS. 16A-16E).

As mentioned, the dose setting mechanism can be designed and configured as a fixed dose device. Alternatively, the dose setting mechanism could allow for setting of one or more user selected doses through the rotation of the dose knob 5 relative to housing 4. Part of the dose setting mechanism of most pen-type injectors is a piston rod 11 that in some cases has a non-circular cross-section with two flat surfaces that are designed to prevent the piston rod from rotating, but allows it to move linearly in the proximal direction. As the piston rod moves proximally it pushes stoppers 25,26 proximally to expel medicament 39. The piston rod 11 is held in a non-rotational state relative to housing 4 during both dose setting and dose delivery because it is arranged within a non-circular pass through hole in the center of a piston rod guide in the case of a fully disposable device or in the piston rod return ring when the device is design as a rescuable device. In either design, during dose setting and dose delivery the piston rod guide or return ring is both rotationally and axially fixed to housing 4. This fixation can be achieved when the piston rod guide is a separate component from the housing 4. The return ring becomes rotational fixed relative to the housing when the cartridge holder is fully attached to the dose setting mechanism.

The priming features described above are applicable to the embodiments shown in FIGS. 11 to 18F. The same is true of the dose canceling procedure.

During dose setting, the dose knob 5 translates out and away from the distal end of housing 4. As the dose dial sleeve rotates and translates distally, the progress of the dose setting (or dose cancellation) is observed in window 7 as printed indicia on the dose dial sleeve moves past the window. When a desired dose setting is reached the indicia for that dose will appear in the window. At this point the injection device 1 is ready for a priming procedure or, if already primed, the delivery of the medicament to an injection site. In either the case, the user will push button 6 on the dose knob in the proximal direction until the zero-dose hard stop is reached and a zero-dose indicia is observed in the window. During a priming step the user will observe whether medicament is expelled out of the cannula of a pen needle. If no medicament is expelled this means the piston rod is not in abutment with the distal face of sliding piston or stopper 25. The priming step is then repeated until medicament is observed exiting the cannula.

The dose setting mechanism of the present disclosure can also have a maximum dose hard stop feature that prevents a user from setting a dose greater than the highest predetermined dose setting.

Once a dose has been dialed on the dose setting mechanism, the user can then exert an axial force in the proximal direction on button 6 to initiate the dose delivery procedure. The axial force exerted by the user overcomes a distally directed force exerted by a biasing member causing the piston rod 11 to move axially in the proximal direction. Axial movement of the piston rod causes the sliding stoppers to also move axially relative to the inside walls of chamber 19 of the stationary cartridge 35 forcing an amount of medicament 39 out of the needle cannula 6 that is equivalent to the dose that was set by the user during the dose setting procedure.

If the device is configured as a disposable injection device, then the cartridge 35 is not replaceable because the connection between the cartridge holder 50 and the housing 4 is permanent. Only through breaking or deformation of this connection can the cartridge be removed from the injection device. Such a disposable device is designed to be thrown out once the medicament has been expelled from the cartridge.

It is to be understood that the embodiments described above and shown in the drawings are to be regarded only as non-limiting examples of the possible designs of the safety assembly and such designs may be modified in many ways within the scope of the patent claims.

What is claimed is:

1. A medicament delivery device for delivery of a medicament mixed within a multi-chambered cartridge, comprising:

a distal part comprising a dose setting mechanism having a housing and a piston rod configured to move axially along a longitudinal axis of the housing during dose delivery;

a proximal part comprising a screw driven sleeve and a cartridge holder configured to accept a multi chambered cartridge, the screw driven sleeve attached to or configured for attachment to the distal part and when the screw driven sleeve is rotated relative to the cartridge holder a medicament mixing process is performed within the multi-chambered cartridge; and a radial stop configured to define a radial position of the cartridge holder relative to the dose setting mechanism after a reconstitution procedure when the medicament delivery device is in a ready-to-use state, the radial stop including a contact surface extending in a direction that is transverse to a radial plane perpendicular to the longitudinal axis.

2. The medicament delivery device of claim 1, wherein the screw driven sleeve has a start position such that the screw driven sleeve extends distally from the cartridge holder.

3. The medicament delivery device of claim 1, wherein the screw driven sleeve has an end position where the screw driven sleeve is retracted proximally into the cartridge holder.

4. The medicament delivery device of claim 1, wherein the screw driven sleeve further comprises a snap arm located on an outside surface.

5. The medicament delivery device of claim 4, wherein an assembly of the cartridge holder, the multi-chambered cartridge and the screw driven sleeve is configured to be disposable, and a protrusion on the snap arm is configured to engage a snap window in a non-releasable and permanent attachment such that the screw driven sleeve is not capable of being rotated relative to the cartridge holder.

6. The medicament delivery device of claim 4, wherein the cartridge holder further comprises snap windows configured to interact and engage with the snap arm.

7. The medicament delivery device of claim 4, wherein when the screw driven sleeve is in a start position, the snap arm is releasably engaged with a first snap window on the cartridge holder or when the medicament mixing process is complete the screw driven sleeve is fully positioned inside the cartridge holder and the snap arm is engaged with a second snap window on the cartridge holder.

8. The medicament delivery device of claim 1, wherein the medicament delivery device is completely disposable.

9. The medicament delivery device of claim 1, wherein the cartridge holder has a cut-out or snap window.

10. The medicament delivery device of claim 9, wherein the cut-out or snap window is configured to interact with a flexible or snap arm located on an outside of the screw driven sleeve.

11. The medicament delivery device of claim 10, wherein the snap arm on the screw driven sleeve has an outward radially extending protrusion configured to engage the cut-out or snap window.

12. The medicament delivery device of claim 10, wherein when the screw driven sleeve is in a start position, the snap arm is releasably engaged with the snap window.

13. The medicament delivery device of claim 10,
wherein, when a reconstitution process is complete, the screw driven sleeve is fully positioned inside the cartridge holder and the snap arm is engaged with the snap window.

14. The medicament delivery device of claim 13,
wherein an engagement of a protrusion with the snap window is non-releasable, such that the screw driven sleeve is not capable of being rotated relative to the cartridge holder.

15. The medicament delivery device of claim 1,
wherein the medicament delivery device is provided to an end user with the cartridge snapped into a cartridge container and the screw driven sleeve snapped into the cartridge holder through engagement of a snap arm with a snap window.

16. The medicament delivery device of claim 1,
further comprising fasteners that cooperate to permanently connect the distal and proximal parts of the medicament delivery device to each other.

17. The medicament delivery device of claim 16,
wherein the fasteners cooperate to form an irreversible snap fit.

18. The medicament delivery device of claim 1,
wherein, once the cartridge holder is fully attached to the dose setting mechanism the connection is fixed, permanent and irreversible, preventing a user from disassembling the cartridge holder from the dose setting mechanism without physically breaking or destroying the medicament delivery device.

19. The medicament delivery device of claim 1,
wherein the cartridge is held in place in the cartridge holder through a snap-in notch that accepts a radially protruding bypass section of the cartridge.

20. The medicament delivery device of claim 1,
wherein the piston rod is configured to exert an axial force in a proximal direction on a distal stopper causing the distal stopper to move proximally relative to an inside wall of the cartridge.

21. The medicament delivery device of claim 20,
wherein the distal stopper is a second stopper, and the force on the second stopper is directly transferred to a first stopper because the liquid solvent in a second chamber is incompressible such that both the first and second stoppers, and the solvent located between them, each move axially forward towards a bypass section of the cartridge.

22. The medicament delivery device of claim 21,
wherein once the first stopper has moved into alignment with the bypass, the solvent is capable of flowing from the second chamber around the first stopper and empty into a first chamber where to contact the lyophilized drug agent and reconstitution begins.

23. The medicament delivery device of claim 22,
wherein as the cartridge holder is configured to rotate and move relative to the screw driven sleeve, the cartridge is configured to move relative to the stationary piston rod, so as to push the second stopper axially in the proximal direction inside the cartridge until all the solvent is forced out of the second chamber and into the first chamber.

24. The medicament delivery device of claim 1,
wherein the distal part comprises a dose setting knob or an injection button.

25. The medicament delivery device of claim 1, wherein the radial stop is disposed at a predefined angular position with respect to the longitudinal axis.

26. A medicament delivery device for delivery of a medicament mixed within a multi-chambered cartridge, comprising:
a distal part comprising a dose setting mechanism having a housing and a piston rod capable of moving axially along a longitudinal axis of the housing during dose delivery; and
a proximal part comprising a screw driven sleeve and a cartridge holder configured to accept a multi-chambered cartridge,
the screw driven sleeve attached to or configured to attach to the distal part,
the screw driven sleeve is configured to rotate relative to the cartridge holder to perform a medicament mixing process within the multi-chambered cartridge,
the cartridge holder having a cut-out or snap window, and
the cut-out or snap window configured to interact with a flexible or snap arm located on an outside of the screw driven sleeve, and when the screw driven sleeve is in a start position, the snap arm is releasably engaged with the snap window.

27. The medicament delivery device of claim 26, wherein the screw driven sleeve has a helical screw thread configured to engage and cooperate with a like thread of the cartridge holder.

* * * * *